United States Patent
Bidney et al.

(10) Patent No.: US 6,709,865 B1
(45) Date of Patent: Mar. 23, 2004

(54) SUNFLOWER LOX POLYNUCLEOTIDES AND RELATED COMPOSITIONS

(75) Inventors: Dennis L. Bidney, Urbandale, IA (US); Jonathan P. Duvick, Des Moines, IA (US); Carol Hendrick, Des Moines, IA (US); Xu Hu, Urbandale, IA (US); Guihua Lu, Urbandale, IA (US); Oswald R. Crasta, Branford, CT (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/714,767

(22) Filed: Nov. 16, 2000

Related U.S. Application Data

(60) Provisional application No. 60/201,837, filed on May 3, 2000, and provisional application No. 60/166,128, filed on Nov. 18, 1999.

(51) Int. Cl.[7] .............................. C12N 5/00; C12N 9/00; C12N 15/00; C12N 15/52

(52) U.S. Cl. .................... 435/419; 536/23.1; 435/320.1

(58) Field of Search ................................ 800/278, 298, 800/322; 536/23.1, 23.2, 23.6; 435/320.1, 410, 416, 419, 468

(56) References Cited

U.S. PATENT DOCUMENTS 5,844,121 A 12/1998 Keller

FOREIGN PATENT DOCUMENTS

| EP | 1 033 405 A2 | 9/2000 |
|---|---|---|
| WO | WO 99/04013 A2 | 1/1999 |

OTHER PUBLICATIONS

Broun et al., Catalytic Plasticity of Fatty Acid Modification Enzymes Underlying Chemical Diversity of Plant Lipids, Nov. 13, 1998, Science, vol. 282, pp. 1315–1317.*
Rance et al., The incompatible interaction between *Phytophthora parasitica* var. nicotiane race 0 and tobacco is suppressed . . . , May 1998, Plant Biology, vol. 95, pp. 6554–6559.*
Bork, Powers and Pitfalls in Sequence Analysis: The 70% Hurdle, 2000, pp. 398–400.*
Skolnick et al., From genes to proteins structure and function novel applications of computational approaches in the genomic era, 2000, Trends in Biotech, vol. 18, No. 1, pp. 34–39.*
Fourgoux–Nicol et al., 1999, Plant Molecular Biology 40 :857–872.*
Broun P. et al. Science vol. 282; Nov. 13, 1998, pp. 1315–1317.*
Barrett et al. (1997) "The Structure of the GTPase–Activating Domain from p50rhoGAP" *Nature* 385:458–461.
Boguski et al. (1994) "Proteins Regulating Ras and Its Relatives" *Nature* 366:643–654.
Borg et al. (1999) "Plant Cell Growth and Differentiation May Involve GAP Regulation of Rac Activity" *FEBS Letters* 453:341–345.
Bourne et al. (1990) "The GTPase Superfamily: A Conserved Switch for Diverse Cell Functions" *Nature* 348:125–132.
De Bruxelles et al. (1996) "Abscisic Acid Induces the Alcohol Dehydrogenase Gene in Arabidopsis" *Plant Physiol.* 111:381–391.
Dolferus et al. (1994) "Differential Interactions of Promoter Elements in Stress Responses of the *Arabidopsis Adh* Gene" *Plant Physiol.* 105:1075–1087.
Dröge–Laser et al. (1997) "Rapid Stimulation of a Soybean Protein–Serine Kinase That Phosphorylates a Novel bZIP DNA–Binding Protein, GHBF–1, during the Induction of Early Transcription–Dependent Defenses" *EMBO J.* 16(4):726–738.
Eulgem et al. (1999) "Early Nuclear Events in Plant Defence Signalling: Rapid Gene Activation by WRKY Transcription Factors" *EMBO J.* 18(17):4689–4699.
Hake et al. (1985) "Coordinate Induction of Alcohol Dehydrogenase 1, Aldolase, and Other Anaerobic RNAs in Maize" *J. Biol. Chem.* 260(8):5050–5054.
Kausch et al. (1997) "Molecular Cloning of a Ripening–Specific Lipoxygenase and Its Expression during Wild–Type and Mutant Tomato Fruit Development" *Plant Physiol.* 113:1041–1050.
Lamarche et al. (1994) "GAPS for rho–related GTPases" *Trends in Genetics* 10(12):436–440.
Lancaster et al. (1994) "Characterization of rhoGAP" *J. Biol. Chem.* 269(2):1137–1142.
Matsui et al. (1999) "Cucumber Cotyledon Lipoxygenase during Postgerminative Growth. Its Expression and Action on Lipid Bodies" *Plant Physiol.* 119:1279–1287.
Mauch et al. (1997) "Mechanosensitive Expression of a Lipoxygenase Gene in Wheat" *Plant Physiol.* 114:1561–1566.
Melan et al. (1993) "An *Arabidopsis thaliana* Lipoxygenase Gene Can by Induced Be Pathogens, Abscisic Acid, and Methyl Jasmonate" *Plant Physiol.* 101:441–450.
Ouwerkerk et al. (1999) "A G–Box Element from the *Catharanthus roseus* Strictosidine Synthase (Str) Gene Promoter Confers Seed–Specific Expression in Transgenic Tobacco Plants" *Mol. Gen. Genet.* 261:635–643.

(List continued on next page.)

Primary Examiner—Amy J. Nelson
Assistant Examiner—Russell Kallis
(74) Attorney, Agent, or Firm—Alston & Bird LLP

(57) ABSTRACT

Methods and compositions for modulating development and defense response are provided. Nucleotide sequences encoding a LOX protein are provided. Nucleotide sequences comprising the LOX promoter are also provided. The sequences can be used in expression cassettes for modulating development, developmental pathways, and the plant defense response. Transformed plants, plant cells, tissues, and seed are also provided.

15 Claims, 2 Drawing Sheets

OTHER PUBLICATIONS

Rancé et al. (1998) "The Incompatible Interaction between *Phytophthora parasitica* var. nicotianae Race 0 and Tobacco Is Suppressed in Transgenic Plants Expressing Antisense Lipoxygenase Sequences" *Proc. Natl. Acad. Sci. USA* 95:6554–6559.

Ridley et al. (1992) "The Small GTP–Binding Protein Rac Regulates Growth Factor–Induced Membrane Ruffling" *Cell* 70:401–410.

Robertson et al. (1995) "Rapid Changes in Oxidative Metabolism as a Consequence of Elicitor Treatment of Suspension–Cultured Cells of French Bean (*Phaseolus vulgaris* L.)" *Plant Mol. Biol.* 27:59–67.

Royo et al. (1996) "Characterization of Three Potato Lipoxygenases with Distinct Enzymatic Activities and Different Organ–Specific and Wound–Regulated Expression Patterns" *J. Biol. Chem.* 271(35):21012–21019.

Royo et al. (1999) "Antisense–Mediated Depletion of a Potato Lipoxygenase Reduces Wound Induction of Proteinase Inhibitors and Increases Weight Gain of Insect Pests" *Proc. Natl. Acad. Sci. USA* 96:1146–1151.

Torres et al. (1976) "Dissociation–Recombination of Intergenic Sunflower Alcohol Dehydrogenase Isozymes and Relative Isozyme Activities" *Biochem. Genet.* 14(1/2):87–98.

Vörös et al. (1998) "Characterization of a Methyljasmonate–Inducible Lipoxygenase from Barley (*Hordeum vulgare* cv. Salome) Leaves" *Eur. J. Biochem.* 251:36–44.

NCBI Accession No. AB017525.
NCBI Accession No. AB017528.
NCBI Accession No. AB024712.
NCBI Accession No. AB027456.
NCBI Accession No. AB027504.
NCBI Accession No. AB077506.
NCBI Accession No. AF064787.
NCBI Accession No. AF145261.
NCBI Accession No. AF159882.
NCBI Accession No. CAA42686.
NCBI Accession No. CAB50064.
NCBI Accession No. D16111.
NCBI Accession No. D87130.
NCBI Accession No. NDPS7A.
NCBI Accession No. O16264.
NCBI Accession No. O84741.
NCBI Accession No. P00331.
NCBI Accession No. P12994.
NCBI Accession No. P16740.
NCBI Accession No. P28032.
NCBI Accession No. P38418.
NCBI Accession No. P38419.
NCBI Accession No. P48977.
NCBI Accession No. P54186.
NCBI Accession No. P77368.
NCBI Accession No. P93698.
NCBI Accession No. Q40249.
NCBI Accession No. Q41261.
NCBI Accession No. Q96573.
NCBI Accession No. U84140.
NCBI Accession No. X54818.
NCBI Accession No. X62362.
NCBI Accession No. Z19625.
NCBI Accession No. Z23024.

U.S. patent application Ser. No. 09/714,071, Duvick et al., filed Nov. 16, 2000.

EMBL Database Report for Accession No. AW031283, Sep. 17, 1999 (XP–002174684).

EMBL Database Report for Accession No. O81806, Nov. 1, 1998 (XP–002174683).

Gentzbittel, L. et al., "Cloning of Molecular Markers for Disease Resistance in Sunflower, *Helianthus Annuus* L.," *Theoretical and Applied Science*, Mar. 1998, pp. 519–525, vol. 96(3), Springer, Germany.

Takai, Y., et al., "Rho as a Regulator of the Cytoskeleton" *Trends in Biochemical Sciences*, Jun. 1995, pp. 227–231, vol. 20(6), Elsevier Science Ltd., United Kingdom.

Winge, P., et al., "Cloning and Characterization of Rac–like cDNAs from *Arabidopsis thaliana*" *Plant Molecular Biology*, 1997, pp. 483–495, vol. 35, Kluwer Academic Publishers, Belgium.

Invitation to Pay Additional Fees with Partial Search Report mailed Aug. 27, 2001 for International Application No. PCT/US00/31187 filed Nov. 13, 2000.

Almoguera, C., and Jordano, J., "Developemental and Environmental Concurrent Expression of Sunflower Dry–Seed Stored Low–Molecular–Weight Heat–Shock Protein and Lea mRNAs," *Plant Molecular Biology*, 1992, pp. 781–792, vol. 19.

EMBL Database Report for Accession No. 081806, Nov. 1, 1998 (XP–002174683).

EMBL Database Report for Accession No. AW031283, Sep. 17, 1999 (XP–002174684).

EMBL Database Report for Accession No. Q9M042, Oct. 1, 2000 (XP–002186562).

EMBL Database Report for Accession No. A1032451, Jun. 24, 1998 (XP–002186563).

EMBL Database Report for Accession No. AU034024, Oct. 28, 1998 (XP–002186564).

Heitz, T., et al., A Gene Encoding a Chloroplast–Targeted Lipoxygenase in Tomato Leaves is Transiently Induced by Wounding, Systemin, and Methyl Jasmonate[1], *Plant Physiol*, 1992, pp. 1085–1093, vol. 114.

Parniske, M., et al., Novel Disease Resistance Specificities Result from Sequence Exchange Between Tandemly Repeated Genes at the Cf–4/9 Locus of Tomato, *Cell*, 1997, pp. 821–832, vol. 91.

* cited by examiner

SEQUENCE LISTING

<160> NUMBER OF SEQ ID NOS: 10

<210> SEQ ID NO 1
<211> LENGTH: 824
<212> TYPE: DNA
<213> ORGANISM: Helianthus annus
<220> FEATURE:
<221> NAME/KEY: misc_feature
<222> LOCATION: (0)...(0)
<223> OTHER INFORMATION: rhoGAP
<220> FEATURE:
<221> NAME/KEY: CDS
<222> LOCATION: (35)...(637)

<400> SEQUENCE: 1

```
ttcggcacga gtccaaatcc aatcttcaat cacc atg gct gaa gaa caa ctg ccg         55
                                    Met Ala Glu Glu Gln Leu Pro
                                     1               5 cct gat caa att aaa ctc att cac aag ctt aat ttg ttc aaa atc aaa          103
Pro Asp Gln Ile Lys Leu Ile His Lys Leu Asn Leu Phe Lys Ile Lys
         10              15                  20 ggc aga gat aaa cac aat cgc aaa atc tta cga att gtc gga aaa aac          151
Gly Arg Asp Lys His Asn Arg Lys Ile Leu Arg Ile Val Gly Lys Asn
 25                  30                  35 ttt cca gct aag agt ttg acc gtt gac ctg ttg aaa aaa tat cta gaa          199
Phe Pro Ala Lys Ser Leu Thr Val Asp Leu Leu Lys Lys Tyr Leu Glu
 40                  45                  50                  55 gtg aaa att ttc ccc aaa ctt gaa cga ccg ttt gtg gtg gtt tac gtt          247
Val Lys Ile Phe Pro Lys Leu Glu Arg Pro Phe Val Val Val Tyr Val
             60                  65                  70 cac act gat gtt cag aag agc gag aat ttc cct gga ata tcc gtt ctc          295
His Thr Asp Val Gln Lys Ser Glu Asn Phe Pro Gly Ile Ser Val Leu
         75                  80                  85 cgg tca gtt tac gac gcg att ccg atg acc gtg aaa caa tat ctt gag          343
Arg Ser Val Tyr Asp Ala Ile Pro Met Thr Val Lys Gln Tyr Leu Glu
         90                  95                 100 gcg gtt tac ttt gtt cat ccg gat ctg cag tcc aga att ttt ctg gct          391
Ala Val Tyr Phe Val His Pro Asp Leu Gln Ser Arg Ile Phe Leu Ala
         105                 110                 115 aca ttt ggc cgg ctt atc ttc acc gga ggg tta tat gca aag ctg aga          439
Thr Phe Gly Arg Leu Ile Phe Thr Gly Gly Leu Tyr Ala Lys Leu Arg
120                 125                 130                 135 ttt gtg agt cga ttg gcg tat ctg tgg gaa cat gtg aaa agg aac gag          487
Phe Val Ser Arg Leu Ala Tyr Leu Trp Glu His Val Lys Arg Asn Glu
             140                 145                 150 atc gag atc cca gag ttt gtc tac gat cat gat gag gat ctg gag tac          535
Ile Glu Ile Pro Glu Phe Val Tyr Asp His Asp Glu Asp Leu Glu Tyr
             155                 160                 165 cgt ccg atg atg gat tac ggg ata gag agt gac cac gct aga gtt tat          583
Arg Pro Met Met Asp Tyr Gly Ile Glu Ser Asp His Ala Arg Val Tyr
         170                 175                 180 gga gcg ccc gcg gtt gat tcc tct gtg gcg gct tat tcc atg agg tgt          631
Gly Ala Pro Ala Val Asp Ser Ser Val Ala Ala Tyr Ser Met Arg Cys
         185                 190                 195 atc tca taggggaaat agttgttttt tcttttgttt ttgaaaatag gtgctaaaag           687
Ile Ser
```

```
Ile Ser
200 aagtgcaata tatagtattt agcaatatt cgggtgttgt agtatgttga taacgggctt    747 ttcttataac attcattgtt ctagttttct tttgtaaaaa ttatttgata aattctttgt    807 aaaaaaaaaa aaaaaaa                                                    824

<210> SEQ ID NO 2
<211> LENGTH: 201
<212> TYPE: PRT
<213> ORGANISM: Helianthus annus

<400> SEQUENCE: 2

Met Ala Glu Glu Gln Leu Pro Pro Asp Gln Ile Lys Leu Ile His Lys
  1               5                  10                  15

Leu Asn Leu Phe Lys Ile Lys Gly Arg Asp Lys His Asn Arg Lys Ile
             20                  25                  30

Leu Arg Ile Val Gly Lys Asn Phe Pro Ala Lys Ser Leu Thr Val Asp
         35                  40                  45

Leu Leu Lys Lys Tyr Leu Glu Val Lys Ile Phe Pro Lys Leu Glu Arg
 50                  55                  60

Pro Phe Val Val Val Tyr Val His Thr Asp Val Gln Lys Ser Glu Asn
 65                  70                  75                  80

Phe Pro Gly Ile Ser Val Leu Arg Ser Val Tyr Asp Ala Ile Pro Met
                 85                  90                  95

Thr Val Lys Gln Tyr Leu Glu Ala Val Tyr Phe Val His Pro Asp Leu
            100                 105                 110

Gln Ser Arg Ile Phe Leu Ala Thr Phe Gly Arg Leu Ile Phe Thr Gly
        115                 120                 125

Gly Leu Tyr Ala Lys Leu Arg Phe Val Ser Arg Leu Ala Tyr Leu Trp
130                 135                 140

Glu His Val Lys Arg Asn Glu Ile Glu Ile Pro Glu Phe Val Tyr Asp
145                 150                 155                 160

His Asp Glu Asp Leu Glu Tyr Arg Pro Met Met Asp Tyr Gly Ile Glu
                165                 170                 175

Ser Asp His Ala Arg Val Tyr Gly Ala Pro Ala Val Asp Ser Ser Val
            180                 185                 190

Ala Ala Tyr Ser Met Arg Cys Ile Ser
        195                 200

<210> SEQ ID NO 3
<211> LENGTH: 2945
<212> TYPE: DNA
<213> ORGANISM: Helianthus annus
<220> FEATURE:
<221> NAME/KEY: misc_feature
<222> LOCATION: (0)...(0)
<223> OTHER INFORMATION: lox cDNA
<220> FEATURE:
<221> NAME/KEY: CDS
<222> LOCATION: (19)...(2721)

<400> SEQUENCE: 3
cggcacgaga agaaaacc atg ttg aat tct caa atc aac cat tct cac cct      51
                    Met Leu Asn Ser Gln Ile Asn His Ser His Pro
                      1               5                  10 ctt aac aac cta cta cca atc cgc aaa gcc ttt gtc cat ggt gac acc     99
Leu Asn Asn Leu Leu Pro Ile Arg Lys Ala Phe Val His Gly Asp Thr
             15                  20                  25
```

```
act aac cat tcc tcc tcc aac gcc tac tcc ccc gcc aac ctt cgc caa      147
Thr Asn His Ser Ser Ser Asn Ala Tyr Ser Pro Ala Asn Leu Arg Gln
        30              35              40 cac gcg tcc acc aag aaa tcc aat gct acc cgt gca cga tcc acc tca      195
His Ala Ser Thr Lys Lys Ser Asn Ala Thr Arg Ala Arg Ser Thr Ser
    45              50              55 act gcg ggt aac att aaa gcc ata tca atc ccc ttt ctt acc aag gag      243
Thr Ala Gly Asn Ile Lys Ala Ile Ser Ile Pro Phe Leu Thr Lys Glu
 60              65              70              75 acc acc gtc aag tgt gtc atc acc gtc caa cca acc att agt tcc gcc      291
Thr Thr Val Lys Cys Val Ile Thr Val Gln Pro Thr Ile Ser Ser Ala
                80              85              90 att gct ggt gta ggc gtt ggt ggt att gtt gat ggt gtt tct gat ctt      339
Ile Ala Gly Val Gly Val Gly Gly Ile Val Asp Gly Val Ser Asp Leu
                95              100             105 cta ggg ttg tca ttt ttg ttg gag ctc gtt tca aat gac ctc gat tca      387
Leu Gly Leu Ser Phe Leu Leu Glu Leu Val Ser Asn Asp Leu Asp Ser
            110             115             120 aaa gga aac caa aag aca gtg aag gct tat gca aga tac aac gca ctg      435
Lys Gly Asn Gln Lys Thr Val Lys Ala Tyr Ala Arg Tyr Asn Ala Leu
        125             130             135 gat ttg gac att agc gtg tac aca tac aaa tgc gac ttc gac gtc cct      483
Asp Leu Asp Ile Ser Val Tyr Thr Tyr Lys Cys Asp Phe Asp Val Pro
140             145             150             155 gaa gat ttt ggg gag ata gga gct gtg ttg gta gaa aat gag tat agc      531
Glu Asp Phe Gly Glu Ile Gly Ala Val Leu Val Glu Asn Glu Tyr Ser
            160             165             170 aag aag atg ttt ttc aag aac att gtt ctt aac aac ggt gtt acc ttc      579
Lys Lys Met Phe Phe Lys Asn Ile Val Leu Asn Asn Gly Val Thr Phe
        175             180             185 aca tgc gag tca tgg gtt cac tcc aaa tac gat aac cct gag aaa aga      627
Thr Cys Glu Ser Trp Val His Ser Lys Tyr Asp Asn Pro Glu Lys Arg
            190             195             200 ata ttt ttc acc gac aag tcg tat cta ccg ttg gaa acg ccg acg gca      675
Ile Phe Phe Thr Asp Lys Ser Tyr Leu Pro Leu Glu Thr Pro Thr Ala
205             210             215 ctg aag ccg tta cga gag aaa gat atg gaa tcg ctt cga gga aac ggc      723
Leu Lys Pro Leu Arg Glu Lys Asp Met Glu Ser Leu Arg Gly Asn Gly
220             225             230             235 gaa gga gaa cgt aaa tca ttc gag cgg ata tat gat tat gat gtg tac      771
Glu Gly Glu Arg Lys Ser Phe Glu Arg Ile Tyr Asp Tyr Asp Val Tyr
            240             245             250 aac gat ctc gga gat ccg gat gga agc tta gat cta gca cgg ccg gtg      819
Asn Asp Leu Gly Asp Pro Asp Gly Ser Leu Asp Leu Ala Arg Pro Val
        255             260             265 ctc ggt ggc gag aca cat ccg tac cct agg cgg tgc cgt act ggt cgc      867
Leu Gly Gly Glu Thr His Pro Tyr Pro Arg Arg Cys Arg Thr Gly Arg
            270             275             280 aaa atg tcc tct aaa gat ccg tta aca gaa agc aga act acg ctc cct      915
Lys Met Ser Ser Lys Asp Pro Leu Thr Glu Ser Arg Thr Thr Leu Pro
285             290             295 ttt tat gta cct gcg gat gaa gat ttt tca gag ata aag agt gtg aac      963
Phe Tyr Val Pro Ala Asp Glu Asp Phe Ser Glu Ile Lys Ser Val Asn
300             305             310             315 ttt gga gca aaa act tta tac tct gtg ctt cat gga gtt gta cca atg      1011
Phe Gly Ala Lys Thr Leu Tyr Ser Val Leu His Gly Val Val Pro Met
            320             325             330 cta gac tca att gta aca gac aaa gac aag ggg ttt cca tta ttc aca      1059
Leu Asp Ser Ile Val Thr Asp Lys Asp Lys Gly Phe Pro Leu Phe Thr
        335             340             345
```

-continued

| | |
|---|---|
| tcc ata gat ttg ctt tat aat gaa ggt gtt aat gtt cct tct cct gac<br>Ser Ile Asp Leu Leu Tyr Asn Glu Gly Val Asn Val Pro Ser Pro Asp<br>350              355              360 | 1107 |
| aat gga att cta agt gct tta cct aga ctt gtc aaa ggg gct act gat<br>Asn Gly Ile Leu Ser Ala Leu Pro Arg Leu Val Lys Gly Ala Thr Asp<br>365              370              375 | 1155 |
| gcc gca aat acc gtt atc aag ttc gag acc ccc gaa acc att gat aga<br>Ala Ala Asn Thr Val Ile Lys Phe Glu Thr Pro Glu Thr Ile Asp Arg<br>380              385              390              395 | 1203 |
| gac gca ttc tca tgg ttc cgt gat gaa gag ttc tgc cgg caa atg ctt<br>Asp Ala Phe Ser Trp Phe Arg Asp Glu Glu Phe Cys Arg Gln Met Leu<br>400              405              410 | 1251 |
| gcc ggt att aat cct tgt cgc ata caa ttg gtt acg gaa tgg cca ttg<br>Ala Gly Ile Asn Pro Cys Arg Ile Gln Leu Val Thr Glu Trp Pro Leu<br>415              420              425 | 1299 |
| atg agt aaa ctg gac cct gaa atc tat gga cca gct gag tca gca att<br>Met Ser Lys Leu Asp Pro Glu Ile Tyr Gly Pro Ala Glu Ser Ala Ile<br>430              435              440 | 1347 |
| aca aag gag att gta gag gaa gag att aaa ggt ttc atg act ctt gag<br>Thr Lys Glu Ile Val Glu Glu Glu Ile Lys Gly Phe Met Thr Leu Glu<br>445              450              455 | 1395 |
| gag gct tta gca caa aag aag ctg ttt atg ctg gat tat cat gat ctg<br>Glu Ala Leu Ala Gln Lys Lys Leu Phe Met Leu Asp Tyr His Asp Leu<br>460              465              470              475 | 1443 |
| ctc ttg cct tat gtt aac aaa acg gag gct gaa ggg aga act ttg tat<br>Leu Leu Pro Tyr Val Asn Lys Thr Glu Ala Glu Gly Arg Thr Leu Tyr<br>480              485              490 | 1491 |
| ggt tca aga act tta atg ttc ctt act cct gct gga aca tta agg cca<br>Gly Ser Arg Thr Leu Met Phe Leu Thr Pro Ala Gly Thr Leu Arg Pro<br>495              500              505 | 1539 |
| cta gcc att gag ctg act cgc cca cca gtt gat ggg aaa cca cag tgg<br>Leu Ala Ile Glu Leu Thr Arg Pro Pro Val Asp Gly Lys Pro Gln Trp<br>510              515              520 | 1587 |
| aaa cat gtt tac aca ccc gct tgg gat gct aca ggt gca tgg ctt tgg<br>Lys His Val Tyr Thr Pro Ala Trp Asp Ala Thr Gly Ala Trp Leu Trp<br>525              530              535 | 1635 |
| aag cta gcc aag gct cat gtc ctt gcc cat gat tct agc tat cac caa<br>Lys Leu Ala Lys Ala His Val Leu Ala His Asp Ser Ser Tyr His Gln<br>540              545              550              555 | 1683 |
| ctt gtt agc cat tgg cta aga aca cat tgt gct acc gaa cct tac att<br>Leu Val Ser His Trp Leu Arg Thr His Cys Ala Thr Glu Pro Tyr Ile<br>560              565              570 | 1731 |
| att gct acc aat cgc caa ctc agt caa atg cat cca att cga cga ttt<br>Ile Ala Thr Asn Arg Gln Leu Ser Gln Met His Pro Ile Arg Arg Phe<br>575              580              585 | 1779 |
| cta ctc cct cat ttc cgt tac act atg caa att aat tct cta gct aga<br>Leu Leu Pro His Phe Arg Tyr Thr Met Gln Ile Asn Ser Leu Ala Arg<br>590              595              600 | 1827 |
| ctt tta ctc gtc aat gcc atg ggt atc ata gag tca aca ttt tct cct<br>Leu Leu Leu Val Asn Ala Met Gly Ile Ile Glu Ser Thr Phe Ser Pro<br>605              610              615 | 1875 |
| gga aga tat tgt atg caa att tcc tct gat gca tat gat cag caa tgg<br>Gly Arg Tyr Cys Met Gln Ile Ser Ser Asp Ala Tyr Asp Gln Gln Trp<br>620              625              630              635 | 1923 |
| cgt ttt gat cat gaa gcg ctt ccg gcc gac cta att agc agg ggt atg<br>Arg Phe Asp His Glu Ala Leu Pro Ala Asp Leu Ile Ser Arg Gly Met<br>640              645              650 | 1971 |
| gcg gtt gaa gat cca acc gca cca tat ggt gta aaa cta aca atc gag<br>Ala Val Glu Asp Pro Thr Ala Pro Tyr Gly Val Lys Leu Thr Ile Glu | 2019 |

|  |  |  |  |  |  |  |  |  |  |  |  |  |  |  |  |
|---|---|---|---|---|---|---|---|---|---|---|---|---|---|---|---|
|  |  |  |  | 655 |  |  |  |  | 660 |  |  |  |  | 665 |  |

```
gat tac cca tat gca aat gat ggt tta ctc att tat gat acc att aaa      2067
Asp Tyr Pro Tyr Ala Asn Asp Gly Leu Leu Ile Tyr Asp Thr Ile Lys
            670                 675                 680 caa tgg gca act tct tat gtc aac cac tat tac cca cca gcg aat cta      2115
Gln Trp Ala Thr Ser Tyr Val Asn His Tyr Tyr Pro Pro Ala Asn Leu
        685                 690                 695 gtg gaa tct gat gaa gag ctt caa gca tgg tgg aat gaa atc cgt aca      2163
Val Glu Ser Asp Glu Glu Leu Gln Ala Trp Trp Asn Glu Ile Arg Thr
700                 705                 710                 715 gtt ggt cat gga gat aag aaa gat gaa cca tgg tgg cca caa ctc aaa      2211
Val Gly His Gly Asp Lys Lys Asp Glu Pro Trp Trp Pro Gln Leu Lys
                720                 725                 730 acc caa gat gat ttg att gga att gtt tca acc atc ttg tgg gtg acc      2259
Thr Gln Asp Asp Leu Ile Gly Ile Val Ser Thr Ile Leu Trp Val Thr
            735                 740                 745 tct ggt caa cat tca gca gtc aac ttc ggt caa tat gat ttc gcg ggt      2307
Ser Gly Gln His Ser Ala Val Asn Phe Gly Gln Tyr Asp Phe Ala Gly
        750                 755                 760 tat ttc cct aac agg ccg aca att tcc aga acc aaa atg ccc aac gaa      2355
Tyr Phe Pro Asn Arg Pro Thr Ile Ser Arg Thr Lys Met Pro Asn Glu
765                 770                 775 gac ccc aca gac gaa gaa tgg cag tcg ttt ata aag cga ccc gag gat      2403
Asp Pro Thr Asp Glu Glu Trp Gln Ser Phe Ile Lys Arg Pro Glu Asp
780                 785                 790                 795 gct tta ttg aaa tgc ttc cca tcc caa atc caa gct aca aaa gtg atg      2451
Ala Leu Leu Lys Cys Phe Pro Ser Gln Ile Gln Ala Thr Lys Val Met
                800                 805                 810 gcg att ttg gat gtt tta tca agt cat tca cca gat gaa gaa tat atc      2499
Ala Ile Leu Asp Val Leu Ser Ser His Ser Pro Asp Glu Glu Tyr Ile
            815                 820                 825 ggt gga aat att gag gcg gca tgg gag gcg gag cct gct ata aaa gca      2547
Gly Gly Asn Ile Glu Ala Ala Trp Glu Ala Glu Pro Ala Ile Lys Ala
        830                 835                 840 gcc ttt gag gag ttc cgt gga agg ctc aat gag ctg gaa gca atc ata      2595
Ala Phe Glu Glu Phe Arg Gly Arg Leu Asn Glu Leu Glu Ala Ile Ile
845                 850                 855 gac tca agg aac acg gat ccc aat ttg aag aat cgt agt ggt gcg ggg      2643
Asp Ser Arg Asn Thr Asp Pro Asn Leu Lys Asn Arg Ser Gly Ala Gly
860                 865                 870                 875 ttg gtt ccg tat caa ctt ctc aaa ccg tat tct gaa aaa ggt gtg acc      2691
Leu Val Pro Tyr Gln Leu Leu Lys Pro Tyr Ser Glu Lys Gly Val Thr
                880                 885                 890 ggg aga ggt gtt cca aac agc ata tcc atc tagttggatt ggtttggttc        2741
Gly Arg Gly Val Pro Asn Ser Ile Ser Ile
            895                 900 ctaatgctcg aggaatagtc tatgtggtgt aataaggcca tgatccatgg tttagttgtg    2801
ttttattgtt atttggaata agttcactta tgtgccttct tgtattataa gccaacatta   2861 tcgaactta tattgtatgt gtattattgt tatttggaat aacatggcat agcaccattc    2921
ttgttaaaaa aaaaaaaaaa aaaa                                          2945
```

<210> SEQ ID NO 4
<211> LENGTH: 901
<212> TYPE: PRT
<213> ORGANISM: Helianthus annus

<400> SEQUENCE: 4

Met Leu Asn Ser Gln Ile Asn His Ser His Pro Leu Asn Asn Leu Leu

-continued

```
1               5                   10                  15

Pro Ile Arg Lys Ala Phe Val His Gly Asp Thr Thr Asn His Ser Ser
                20              25              30

Ser Asn Ala Tyr Ser Pro Ala Asn Leu Arg Gln His Ala Ser Thr Lys
            35              40              45

Lys Ser Asn Ala Thr Arg Ala Arg Ser Thr Ser Thr Ala Gly Asn Ile
        50              55              60

Lys Ala Ile Ser Ile Pro Phe Leu Thr Lys Glu Thr Thr Val Lys Cys
65              70              75              80

Val Ile Thr Val Gln Pro Thr Ile Ser Ser Ala Ile Ala Gly Val Gly
                85              90              95

Val Gly Gly Ile Val Asp Gly Val Ser Asp Leu Leu Gly Leu Ser Phe
            100             105             110

Leu Leu Glu Leu Val Ser Asn Asp Leu Asp Ser Lys Gly Asn Gln Lys
        115             120             125

Thr Val Lys Ala Tyr Ala Arg Tyr Asn Ala Leu Asp Leu Asp Ile Ser
    130             135             140

Val Tyr Thr Tyr Lys Cys Asp Phe Asp Val Pro Glu Asp Phe Gly Glu
145             150             155             160

Ile Gly Ala Val Leu Val Glu Asn Glu Tyr Ser Lys Lys Met Phe Phe
                165             170             175

Lys Asn Ile Val Leu Asn Asn Gly Val Thr Phe Thr Cys Glu Ser Trp
            180             185             190

Val His Ser Lys Tyr Asp Asn Pro Glu Lys Arg Ile Phe Phe Thr Asp
        195             200             205

Lys Ser Tyr Leu Pro Leu Glu Thr Pro Thr Ala Leu Lys Pro Leu Arg
    210             215             220

Glu Lys Asp Met Glu Ser Leu Arg Gly Asn Gly Glu Gly Glu Arg Lys
225             230             235             240

Ser Phe Glu Arg Ile Tyr Asp Tyr Asp Val Tyr Asn Asp Leu Gly Asp
                245             250             255

Pro Asp Gly Ser Leu Asp Leu Ala Arg Pro Val Leu Gly Gly Glu Thr
            260             265             270

His Pro Tyr Pro Arg Arg Cys Arg Thr Gly Arg Lys Met Ser Ser Lys
        275             280             285

Asp Pro Leu Thr Glu Ser Arg Thr Thr Leu Pro Phe Tyr Val Pro Ala
    290             295             300

Asp Glu Asp Phe Ser Glu Ile Lys Ser Val Asn Phe Gly Ala Lys Thr
305             310             315             320

Leu Tyr Ser Val Leu His Gly Val Val Pro Met Leu Asp Ser Ile Val
                325             330             335

Thr Asp Lys Asp Lys Gly Phe Pro Leu Phe Thr Ser Ile Asp Leu Leu
            340             345             350

Tyr Asn Glu Gly Val Asn Val Pro Ser Pro Asp Asn Gly Ile Leu Ser
        355             360             365

Ala Leu Pro Arg Leu Val Lys Gly Ala Thr Asp Ala Asn Thr Val
    370             375             380

Ile Lys Phe Glu Thr Pro Glu Thr Ile Asp Arg Asp Ala Phe Ser Trp
385             390             395             400

Phe Arg Asp Glu Glu Phe Cys Arg Gln Met Leu Ala Gly Ile Asn Pro
                405             410             415

Cys Arg Ile Gln Leu Val Thr Glu Trp Pro Leu Met Ser Lys Leu Asp
            420             425             430
```

-continued

```
Pro Glu Ile Tyr Gly Pro Ala Glu Ser Ala Ile Thr Lys Glu Ile Val
            435                 440                 445

Glu Glu Glu Ile Lys Gly Phe Met Thr Leu Glu Glu Ala Leu Ala Gln
    450                 455                 460

Lys Lys Leu Phe Met Leu Asp Tyr His Asp Leu Leu Pro Tyr Val
465                 470                 475                 480

Asn Lys Thr Glu Ala Glu Gly Arg Thr Leu Tyr Gly Ser Arg Thr Leu
                485                 490                 495

Met Phe Leu Thr Pro Ala Gly Thr Leu Arg Pro Leu Ala Ile Glu Leu
            500                 505                 510

Thr Arg Pro Pro Val Asp Gly Lys Pro Gln Trp Lys His Val Tyr Thr
        515                 520                 525

Pro Ala Trp Asp Ala Thr Gly Ala Trp Leu Trp Lys Leu Ala Lys Ala
        530                 535                 540

His Val Leu Ala His Asp Ser Ser Tyr His Gln Leu Val Ser His Trp
545                 550                 555                 560

Leu Arg Thr His Cys Ala Thr Glu Pro Tyr Ile Ile Ala Thr Asn Arg
                565                 570                 575

Gln Leu Ser Gln Met His Pro Ile Arg Arg Phe Leu Leu Pro His Phe
            580                 585                 590

Arg Tyr Thr Met Gln Ile Asn Ser Leu Ala Arg Leu Leu Leu Val Asn
        595                 600                 605

Ala Met Gly Ile Ile Glu Ser Thr Phe Ser Pro Gly Arg Tyr Cys Met
        610                 615                 620

Gln Ile Ser Ser Asp Ala Tyr Asp Gln Gln Trp Arg Phe Asp His Glu
625                 630                 635                 640

Ala Leu Pro Ala Asp Leu Ile Ser Arg Gly Met Ala Val Glu Asp Pro
                645                 650                 655

Thr Ala Pro Tyr Gly Val Lys Leu Thr Ile Glu Asp Tyr Pro Tyr Ala
            660                 665                 670

Asn Asp Gly Leu Leu Ile Tyr Asp Thr Ile Lys Gln Trp Ala Thr Ser
        675                 680                 685

Tyr Val Asn His Tyr Tyr Pro Pro Ala Asn Leu Val Glu Ser Asp Glu
        690                 695                 700

Glu Leu Gln Ala Trp Trp Asn Glu Ile Arg Thr Val Gly His Gly Asp
705                 710                 715                 720

Lys Lys Asp Glu Pro Trp Trp Pro Gln Leu Lys Thr Gln Asp Asp Leu
                725                 730                 735

Ile Gly Ile Val Ser Thr Ile Leu Trp Val Thr Ser Gly Gln His Ser
            740                 745                 750

Ala Val Asn Phe Gly Gln Tyr Asp Phe Ala Gly Tyr Phe Pro Asn Arg
        755                 760                 765

Pro Thr Ile Ser Arg Thr Lys Met Pro Asn Glu Asp Pro Thr Asp Glu
        770                 775                 780

Glu Trp Gln Ser Phe Ile Lys Arg Pro Glu Asp Ala Leu Leu Lys Cys
785                 790                 795                 800

Phe Pro Ser Gln Ile Gln Ala Thr Lys Val Met Ala Ile Leu Asp Val
                805                 810                 815

Leu Ser Ser His Ser Pro Asp Glu Glu Tyr Ile Gly Gly Asn Ile Glu
            820                 825                 830

Ala Ala Trp Glu Ala Glu Pro Ala Ile Lys Ala Ala Phe Glu Glu Phe
        835                 840                 845
```

```
Arg Gly Arg Leu Asn Glu Leu Glu Ala Ile Ile Asp Ser Arg Asn Thr
    850                 855                 860

Asp Pro Asn Leu Lys Asn Arg Ser Gly Ala Gly Leu Val Pro Tyr Gln
865                 870                 875                 880

Leu Leu Lys Pro Tyr Ser Glu Lys Gly Val Thr Gly Arg Gly Val Pro
                885                 890                 895

Asn Ser Ile Ser Ile
            900

<210> SEQ ID NO 5
<211> LENGTH: 883
<212> TYPE: DNA
<213> ORGANISM: Helianthus annus
<220> FEATURE:
<221> NAME/KEY: promoter
<222> LOCATION: (1)...(880)
<223> OTHER INFORMATION: lox promoter
<220> FEATURE:
<221> NAME/KEY: misc_feature
<222> LOCATION: (322)...(327)
<223> OTHER INFORMATION: W-box
<220> FEATURE:
<221> NAME/KEY: misc_feature
<222> LOCATION: (722)...(727)
<223> OTHER INFORMATION: G-box
<220> FEATURE:
<221> NAME/KEY: misc_feature
<222> LOCATION: (808)...(901)
<223> OTHER INFORMATION: TATA box

<400> SEQUENCE: 5
agggcacgcg tggtcgacgg accgggctgg gtatctcatt catcttagct cggttttgga      60
cgtggtttag ttcgttgcgt acctcttcca acatagaaca caaacccaca ataagtaca     120 taaaacccgc tcattttatt agatttattt ctagtccaaa atacgaaaaa atcattgtcc    180
tatatttgtg aaaaatgcta ttttcactta tttttccaac aacacataca cagagagggc    240
aacaatcggt taacaaactc accagagttg tgaaaattat gaggacttct atctgtcatg    300 caattttta tatatttcct tttgaccaaa acatgtatac atgactaact aaaaatatag     360
ttgcgagttg gaaaagggtt atacactata actcatattt acacaatatt gccttgaaca    420
ttattaacta attacgcggt gttgaataat tttgataaaa acttttctat gtgttgaggt    480
atatctgaac tattaaaata aataccatta atacttcaag attataacat gagaacatta    540
catatattgt gatttatat tataatttaa taattatttt ttttgaaag gcataattta      600 ataattataa gcgacaatac ttctacgttt atagtactag gtactttttc caacccacaa    660
tcaaatgcat tctagccgta gattgtaaat tattaatgca accctgaaca ataatgcata    720
acacgtgaaa tcaatgcaga aatgtatcat tcttatccga tgttttccca ttaaataaaa    780
accttaaaat atagcacatt tcctctctat aaatagagct attttttcaa cttccagatc    840
acacaaaaca agagtgagag tagagtgact aaagaaaacc atg                      883

<210> SEQ ID NO 6
<211> LENGTH: 1403
<212> TYPE: DNA
<213> ORGANISM: Helianthus annus
<220> FEATURE:
<221> NAME/KEY: misc_feature
<222> LOCATION: (0)...(0)
<223> OTHER INFORMATION: ADH cDNA
<220> FEATURE:
<221> NAME/KEY: CDS
<222> LOCATION: (74)...(1216)
```

<400> SEQUENCE: 6

```
ttcggcacga gccaaaactc acaatttaat ctcatttcaa gaatattctc tctttcaccg      60
```

| | | | | | | | | | | | | | | | |
|---|---|---|---|---|---|---|---|---|---|---|---|---|---|---|---|
| atcaaacaaa agt | atg | tcg | tcg | acc | act | aca | ggc | caa | gtt | att | cga | tgc | | | 109 |
| | Met | Ser | Ser | Thr | Thr | Thr | Gly | Gln | Val | Ile | Arg | Cys | | | |
| | 1 | | | 5 | | | | | 10 | | | | | | |
| aaa | gcc | gcg | gtg | acg | tgg | gaa | gcc | gga | aaa | ccg | ctg | gtg | atc | gaa gaa | 157 |
| Lys | Ala | Ala | Val | Thr | Trp | Glu | Ala | Gly | Lys | Pro | Leu | Val | Ile | Glu Glu | |
| | 15 | | | | 20 | | | | | 25 | | | | | |
| gtg | gag | gtg | gcg | cca | ccg | cag | aaa | atg | gaa | gtc | cgg | att | aag | atc ctc | 205 |
| Val | Glu | Val | Ala | Pro | Pro | Gln | Lys | Met | Glu | Val | Arg | Ile | Lys | Ile Leu | |
| 30 | | | | | 35 | | | | | 40 | | | | | |
| ttc | act | tcc | ctc | tgc | cac | act | gat | gtt | tac | ttc | tgg | gaa | gcc | aaa gga | 253 |
| Phe | Thr | Ser | Leu | Cys | His | Thr | Asp | Val | Tyr | Phe | Trp | Glu | Ala | Lys Gly | |
| 45 | | | | 50 | | | | | 55 | | | | | 60 | |
| caa | aat | cct | gta | ttc | cca | aga | att | tta | gga | cat | gaa | gct | gga | ggg gtt | 301 |
| Gln | Asn | Pro | Val | Phe | Pro | Arg | Ile | Leu | Gly | His | Glu | Ala | Gly | Gly Val | |
| | | | | 65 | | | | | 70 | | | | | 75 | |
| gtg | gag | agt | gtt | ggg | gaa | gga | gtg | act | gat | ctt | cag | cca | ggg | gat cat | 349 |
| Val | Glu | Ser | Val | Gly | Glu | Gly | Val | Thr | Asp | Leu | Gln | Pro | Gly | Asp His | |
| | | 80 | | | | | 85 | | | | | 90 | | | |
| gtt | ctt | ccc | gtt | ttc | acc | gga | gaa | tgc | aaa | gag | tgt | gct | cac | tgt aag | 397 |
| Val | Leu | Pro | Val | Phe | Thr | Gly | Glu | Cys | Lys | Glu | Cys | Ala | His | Cys Lys | |
| | 95 | | | | 100 | | | | | 105 | | | | | |
| tcc | gaa | gag | agc | aac | atg | tgt | gac | ctt | ctc | agg | atc | aac | acc | gac agg | 445 |
| Ser | Glu | Glu | Ser | Asn | Met | Cys | Asp | Leu | Leu | Arg | Ile | Asn | Thr | Asp Arg | |
| 110 | | | | | 115 | | | | | 120 | | | | | |
| gga | gtc | atg | ctt | cac | gat | cag | aaa | tct | cga | ttc | tcg | atc | aac | ggc aaa | 493 |
| Gly | Val | Met | Leu | His | Asp | Gln | Lys | Ser | Arg | Phe | Ser | Ile | Asn | Gly Lys | |
| 125 | | | | 130 | | | | | 135 | | | | | 140 | |
| ccc | atc | ttc | cat | ttt | gtg | ggg | act | tct | act | ttc | agc | gag | tac | acg gtt | 541 |
| Pro | Ile | Phe | His | Phe | Val | Gly | Thr | Ser | Thr | Phe | Ser | Glu | Tyr | Thr Val | |
| | | | | 145 | | | | | 150 | | | | | 155 | |
| gtt | cat | gtt | gga | tgt | ctt | gca | aag | atc | aac | cct | ctt | gcc | cct | ctt gat | 589 |
| Val | His | Val | Gly | Cys | Leu | Ala | Lys | Ile | Asn | Pro | Leu | Ala | Pro | Leu Asp | |
| | | | 160 | | | | | 165 | | | | | 170 | | |
| aaa | gtt | tgt | gtt | ctc | agc | tgt | ggg | atc | tcc | aca | ggg | ctg | ggt | gct act | 637 |
| Lys | Val | Cys | Val | Leu | Ser | Cys | Gly | Ile | Ser | Thr | Gly | Leu | Gly | Ala Thr | |
| | | 175 | | | | | 180 | | | | | 185 | | | |
| ttg | aat | gtt | gca | aaa | ccg | aaa | aaa | ggc | tct | tcg | gtg | gcg | gtt | ttc ggt | 685 |
| Leu | Asn | Val | Ala | Lys | Pro | Lys | Lys | Gly | Ser | Ser | Val | Ala | Val | Phe Gly | |
| | 190 | | | | | 195 | | | | | 200 | | | | |
| ctg | ggg | gca | gtg | gga | ctt | gct | gct | gct | gaa | ggt | gca | aga | att | tct ggg | 733 |
| Leu | Gly | Ala | Val | Gly | Leu | Ala | Ala | Ala | Glu | Gly | Ala | Arg | Ile | Ser Gly | |
| 205 | | | | 210 | | | | | 215 | | | | | 220 | |
| gct | tca | aga | atc | att | ggt | gtt | gat | ctc | aat | gcc | aat | aga | ttc | gag ctt | 781 |
| Ala | Ser | Arg | Ile | Ile | Gly | Val | Asp | Leu | Asn | Ala | Asn | Arg | Phe | Glu Leu | |
| | | | | 225 | | | | | 230 | | | | | 235 | |
| gca | aag | aaa | ttt | ggg | gtt | aca | gag | ttt | gtg | aac | cca | aaa | gat | tat aag | 829 |
| Ala | Lys | Lys | Phe | Gly | Val | Thr | Glu | Phe | Val | Asn | Pro | Lys | Asp | Tyr Lys | |
| | | | 240 | | | | | 245 | | | | | 250 | | |
| aag | ccg | gtg | caa | gaa | gtg | att | gca | gag | atg | aca | aat | gga | gga | gtt gac | 877 |
| Lys | Pro | Val | Gln | Glu | Val | Ile | Ala | Glu | Met | Thr | Asn | Gly | Gly | Val Asp | |
| | | 255 | | | | | 260 | | | | | 265 | | | |
| agg | agt | gtt | gaa | tgc | act | ggt | cat | att | gat | gct | atg | atc | tct | gct ttt | 925 |
| Arg | Ser | Val | Glu | Cys | Thr | Gly | His | Ile | Asp | Ala | Met | Ile | Ser | Ala Phe | |
| | 270 | | | | | 275 | | | | | 280 | | | | |
| gaa | tgt | gtt | cat | gat | ggg | tgg | ggt | gtt | gct | gtt | cta | gta | ggt | gtt ccg | 973 |
| Glu | Cys | Val | His | Asp | Gly | Trp | Gly | Val | Ala | Val | Leu | Val | Gly | Val Pro | |
| 285 | | | | | 290 | | | | | 295 | | | | | 300 |

```
cat aaa gat gcc gtg ttc aag acc agt ccc atg aat ctg ttg aac gaa    1021
His Lys Asp Ala Val Phe Lys Thr Ser Pro Met Asn Leu Leu Asn Glu
            305                 310                 315 agg act ctg aag ggt acc ttc ttt gga aac tat aaa ccg cga tct gat    1069
Arg Thr Leu Lys Gly Thr Phe Phe Gly Asn Tyr Lys Pro Arg Ser Asp
            320                 325                 330 att cct tcg gtt gtc gaa aag tat atg aac aag gaa ctt gag gtg gag    1117
Ile Pro Ser Val Val Glu Lys Tyr Met Asn Lys Glu Leu Glu Val Glu
            335                 340                 345 aag ttc ata aca cat gaa gtg cca ttt tca gag atc aat aag ccc ttt    1165
Lys Phe Ile Thr His Glu Val Pro Phe Ser Glu Ile Asn Lys Pro Phe
        350                 355                 360 gac ttg atg ctt aaa ggt gaa ggt ctt cgt tgc att att cga atg gat    1213
Asp Leu Met Leu Lys Gly Glu Gly Leu Arg Cys Ile Ile Arg Met Asp
365                 370                 375                 380 gcc taaataattt caaactgtgc aagagagagc agtaggagtc gtctattcgt        1266
Ala aaagatatat gtgtgtgttc tcgtctctca tcgtcgtaaa tgtgtcctta agatcttggt  1326
ttgttaattg ttacccataa aagattttga atttgaataa caatagaaat tgatgtctaa  1386
aaaaaaaaaa aaaaaaa                                                 1403

<210> SEQ ID NO 7
<211> LENGTH: 381
<212> TYPE: PRT
<213> ORGANISM: Helianthus annus ADH

<400> SEQUENCE: 7

Met Ser Ser Thr Thr Gly Gln Val Ile Arg Cys Lys Ala Ala Val
1               5                   10                  15

Thr Trp Glu Ala Gly Lys Pro Leu Val Ile Glu Glu Val Glu Val Ala
            20                  25                  30

Pro Pro Gln Lys Met Glu Val Arg Ile Lys Ile Leu Phe Thr Ser Leu
        35                  40                  45

Cys His Thr Asp Val Tyr Phe Trp Glu Ala Lys Gly Gln Asn Pro Val
    50                  55                  60

Phe Pro Arg Ile Leu Gly His Glu Ala Gly Val Val Glu Ser Val
65                  70                  75                  80

Gly Glu Gly Val Thr Asp Leu Gln Pro Gly Asp His Val Leu Pro Val
                85                  90                  95

Phe Thr Gly Glu Cys Lys Glu Cys Ala His Cys Lys Ser Glu Glu Ser
            100                 105                 110

Asn Met Cys Asp Leu Leu Arg Ile Asn Thr Asp Arg Gly Val Met Leu
        115                 120                 125

His Asp Gln Lys Ser Arg Phe Ser Ile Asn Gly Lys Pro Ile Phe His
    130                 135                 140

Phe Val Gly Thr Ser Thr Phe Ser Glu Tyr Thr Val His Val Gly
145                 150                 155                 160

Cys Leu Ala Lys Ile Asn Pro Leu Ala Pro Leu Asp Lys Val Cys Val
                165                 170                 175

Leu Ser Cys Gly Ile Ser Thr Gly Leu Gly Ala Thr Leu Asn Val Ala
            180                 185                 190

Lys Pro Lys Lys Gly Ser Ser Val Ala Val Phe Gly Leu Gly Ala Val
        195                 200                 205

Gly Leu Ala Ala Ala Glu Gly Ala Arg Ile Ser Gly Ala Ser Arg Ile
    210                 215                 220
```

```
Ile Gly Val Asp Leu Asn Ala Asn Arg Phe Glu Leu Ala Lys Lys Phe
225                 230                 235                 240

Gly Val Thr Glu Phe Val Asn Pro Lys Asp Tyr Lys Lys Pro Val Gln
            245                 250                 255

Glu Val Ile Ala Glu Met Thr Asn Gly Gly Val Asp Arg Ser Val Glu
            260                 265                 270

Cys Thr Gly His Ile Asp Ala Met Ile Ser Ala Phe Glu Cys Val His
            275                 280                 285

Asp Gly Trp Gly Val Ala Val Leu Val Gly Val Pro His Lys Asp Ala
290                 295                 300

Val Phe Lys Thr Ser Pro Met Asn Leu Leu Asn Glu Arg Thr Leu Lys
305                 310                 315                 320

Gly Thr Phe Phe Gly Asn Tyr Lys Pro Arg Ser Asp Ile Pro Ser Val
            325                 330                 335

Val Glu Lys Tyr Met Asn Lys Glu Leu Glu Val Glu Lys Phe Ile Thr
            340                 345                 350

His Glu Val Pro Phe Ser Glu Ile Asn Lys Pro Phe Asp Leu Met Leu
            355                 360                 365

Lys Gly Glu Gly Leu Arg Cys Ile Ile Arg Met Asp Ala
370                 375                 380

<210> SEQ ID NO 8
<211> LENGTH: 747
<212> TYPE: DNA
<213> ORGANISM: Helianthus annus
<220> FEATURE:
<221> NAME/KEY: misc_feature
<222> LOCATION: (0)...(0)
<223> OTHER INFORMATION: SCIP-1 cDNA
<220> FEATURE:
<221> NAME/KEY: CDS
<222> LOCATION: (15)...(518)

<400> SEQUENCE: 8
ttcggcacga gcaa atg gcg aac gca agc gat gag ttc aga cta gcg tct        50
                Met Ala Asn Ala Ser Asp Glu Phe Arg Leu Ala Ser
                  1               5                  10 tcc ggc atc gat cat gaa ggc cga cta cca cga aaa tac acc ggt gac        98
Ser Gly Ile Asp His Glu Gly Arg Leu Pro Arg Lys Tyr Thr Gly Asp
        15                  20                  25 ggt caa ggt aca aaa aaa gac ata tca cca ccg tta gaa tgg tac aac       146
Gly Gln Gly Thr Lys Lys Asp Ile Ser Pro Pro Leu Glu Trp Tyr Asn
 30                  35                  40 gtt ccg gag ggg aca aaa aca cta gca cta gtg gtg gag gac atc gat       194
Val Pro Glu Gly Thr Lys Thr Leu Ala Leu Val Val Glu Asp Ile Asp
 45                  50                  55                  60 gca ccg gac cca gaa gcg ccg ctg gtt ccg tgg act gtg tgg gtg gtg       242
Ala Pro Asp Pro Glu Ala Pro Leu Val Pro Trp Thr Val Trp Val Val
                 65                  70                  75 gtc aat ata cca cct act ttg aag ggg ctc cca gag gga ttt tcc ggg       290
Val Asn Ile Pro Pro Thr Leu Lys Gly Leu Pro Glu Gly Phe Ser Gly
             80                  85                  90 aaa gag ggg gac atg ggt ggc gat tat gct aat gtt aaa gaa gga cat       338
Lys Glu Gly Asp Met Gly Gly Asp Tyr Ala Asn Val Lys Glu Gly His
         95                 100                 105 aat gac ttt aag gtg cct gga tgg cgc gca ccg aag atg ccc tca tcc       386
Asn Asp Phe Lys Val Pro Gly Trp Arg Ala Pro Lys Met Pro Ser Ser
    110                 115                 120 gga cac cgg ttc gag ttt aag ctg tat gcg ttg gat gaa caa gtt gag       434
```

```
Gly His Arg Phe Glu Phe Lys Leu Tyr Ala Leu Asp Glu Gln Val Glu
125                 130                 135                 140 ttg ggg aat aag gtg act aag gag aag ttg ctg gag gcg att gat ggc        482
Leu Gly Asn Lys Val Thr Lys Glu Lys Leu Leu Glu Ala Ile Asp Gly
                145                 150                 155 cat gtg gtt ggg gag gct gtt ctg atg gcc gta aat taaattgaga             528
His Val Val Gly Glu Ala Val Leu Met Ala Val Asn
            160                 165 atggtttata tatatgttag ttgtgtgact tgtgtcatgt gtgatgttct tgttttaacg       588
tattttgaaa cagaagtgac gagagagaga gagtgtttgt tgtgtgtttt tcttgagaga       648
tcgtgaatta attatgctgt tttgcttcaa ggaatcaagc tttataaagt aaaatacaaa       708
tgtaatgctt caaccgagct aaaaaaaaaa aaaaaaaa                               747

<210> SEQ ID NO 9
<211> LENGTH: 168
<212> TYPE: PRT
<213> ORGANISM: Helianthus annus SCIP-1

<400> SEQUENCE: 9

Met Ala Asn Ala Ser Asp Glu Phe Arg Leu Ala Ser Ser Gly Ile Asp
1               5                   10                  15

His Glu Gly Arg Leu Pro Arg Lys Tyr Thr Gly Asp Gly Gln Gly Thr
            20                  25                  30

Lys Lys Asp Ile Ser Pro Pro Leu Glu Trp Tyr Asn Val Pro Glu Gly
        35                  40                  45

Thr Lys Thr Leu Ala Leu Val Val Glu Asp Ile Asp Ala Pro Asp Pro
    50                  55                  60

Glu Ala Pro Leu Val Pro Trp Thr Val Trp Val Val Asn Ile Pro
65                  70                  75                  80

Pro Thr Leu Lys Gly Leu Pro Glu Gly Phe Ser Gly Lys Glu Gly Asp
                85                  90                  95

Met Gly Gly Asp Tyr Ala Asn Val Lys Glu Gly His Asn Asp Phe Lys
            100                 105                 110

Val Pro Gly Trp Arg Ala Pro Lys Met Pro Ser Ser Gly His Arg Phe
        115                 120                 125

Glu Phe Lys Leu Tyr Ala Leu Asp Glu Gln Val Glu Leu Gly Asn Lys
    130                 135                 140

Val Thr Lys Glu Lys Leu Leu Glu Ala Ile Asp Gly His Val Val Gly
145                 150                 155                 160

Glu Ala Val Leu Met Ala Val Asn
                165

<210> SEQ ID NO 10
<211> LENGTH: 513
<212> TYPE: DNA
<213> ORGANISM: Helianthus annus
<220> FEATURE:
<221> NAME/KEY: promoter
<222> LOCATION: (1)...(510)
<223> OTHER INFORMATION: SCIP promoter
<220> FEATURE:
<221> NAME/KEY: misc_feature
<222> LOCATION: (364)...(368)
<223> OTHER INFORMATION: W-box
<220> FEATURE:
<221> NAME/KEY: misc_feature
<222> LOCATION: (371)...(375)
<223> OTHER INFORMATION: W-box
<220> FEATURE:
<221> NAME/KEY: misc_feature
```

-continued

```
<222> LOCATION: (415)...(420)
<223> OTHER INFORMATION: G-box

<400> SEQUENCE: 10
cttccctatt ttcggtaaca cttgtgcggc aaagggttg gcagtggtta ccgctcggtg      60
ccgaaccact ttgccgctgc cactccgggc agcctaaata atgctatata tgtgacattt    120
ttgcactgaa ttctactttt tatttaccat acgcgatgaa aaggcattgg ttttttatta    180
tattatattt cagtttctat ttttggacgg caaaaatgaa ttttattaaa agtaaacgaa    240
tttaaaaata ttcggataat tacttttct tttgaatctt gattcggata agttgttacg     300
aattttaaaa cgacaattga ttgaaaatga gtgatgtagc tctttctagc gtaccacgta    360
tctgtcaagt gtcaacatgc tacagcttct caaaactgct agaactctta actacacgtg    420
tccacaaacc cacaaaatcc taaccatcca taacactata agaacttgat caacagatct    480
gtttagtaac aagttattga aggtacaaca atg                                  513
```

SUNFLOWER LOX POLYNUCLEOTIDES AND RELATED COMPOSITIONS

CROSS REFERENCE TO RELATED APPLICATIONS

This application claims the benefit of U.S. Provisional Application No. 60/201,837, filed on May 3, 2000 and U.S. Provisional Application No. 60/166,128, filed on Nov. 18, 1999.

FIELD OF THE INVENTION

The invention relates to the field of the genetic manipulation of plants, particularly the modulation of gene activity and development in plants and increased disease resistance.

BACKGROUND OF THE INVENTION

Disease in plants is caused by biotic and abiotic causes. Biotic causes include fungi, viruses, bacteria, and nematodes. An example of the importance of plant disease is illustrated by phytopathogenic fungi, which cause significant annual crop yield losses as well as devastating epidemics. Plant disease outbreaks have resulted in catastrophic crop failures that have triggered famines and caused major social change. Pathogenic fungi attack all of the approximately 300,000 species of flowering plants, however, a single plant species can be host to only a few fungal species, and similarly, most fungi usually have a limited host range. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Molecular methods of crop protection have the potential to implement novel mechanisms for disease resistance and can also be implemented more quickly than traditional breeding methods. Accordingly, molecular methods are needed to supplement traditional breeding methods to protect plants from pathogen attack.

A host of cellular processes enable plants to defend themselves against disease caused by pathogenic agents. These defense mechanisms are activated by initial pathogen infection in a process known as elicitation. In elicitation, the host plant recognizes a pathogen-derived compound known as an elicitor; the plant then activates disease gene expression to limit further spread of the invading microorganism. It is generally believed that to overcome these plant defense mechanisms, plant pathogens must find a way to suppress elicitation as well as to overcome more physically-based barriers to infection, such as reinforcement and/or rearrangement of the actin filament networks near the cell's plasma membrane.

Thus, the present invention solves needs for enhancement of the plant's defensive elicitation response via a molecularly based mechanism that can be quickly incorporated into commercial crops.

SUMMARY OF THE INVENTION

The present invention provides nucleotide sequences that may find use in modulating development, developmental pathways, and the plant pathogen defense system. Particularly, the nucleotide and amino acid sequences for a sunflower rhoGTPase-Activating Protein (rhoGAP), Lipoxygenase (LOX), Alcohol Dehydrogenase (ADH), and Sclerotinia-Inducible Protein-1 (SCIP-1) are provided.

In particular, the methods and compositions can be used to modulate plant development. More specifically, methods and compositions of the invention may be used for enhancing resistance to plant pathogens including fungal pathogens, plant viruses, and the like. The method involves stably transforming a plant with a nucleotide sequence capable of modulating the plant pathogen defense system operably linked with a promoter capable of driving expression of a gene in a plant cell. The disease resistance genes of the present invention additionally find use in manipulating these processes in transformed plants and plant cells.

Transformed plants, plant cells, and seeds, as well as methods for making such plants, plant cells, and seeds are additionally provided. It is recognized that a variety of promoters will be useful in the invention, the choice of which will depend in part upon the desired level of expression of the disclosed nucleotide sequences. It is recognized that the levels of expression can be controlled to modulate the levels of expression in the plant cell.

Methods and compositions for regulating gene expression in a plant are also provided. Novel nucleotide sequences for inducible plant promoters derived from the LOX and SCIP-1 genes are provided. The methods comprise transforming a plant with a nucleotide sequence of interest operably linked to the LOX or SCIP-1 promoters. Exposure of the transformed plant to a stimulus activates, within the exposed tissue of the plant, transcription of the nucleotide sequence of interest.

DETAILED DESCRIPTION OF THE INVENTION

Overview

Figure 1:
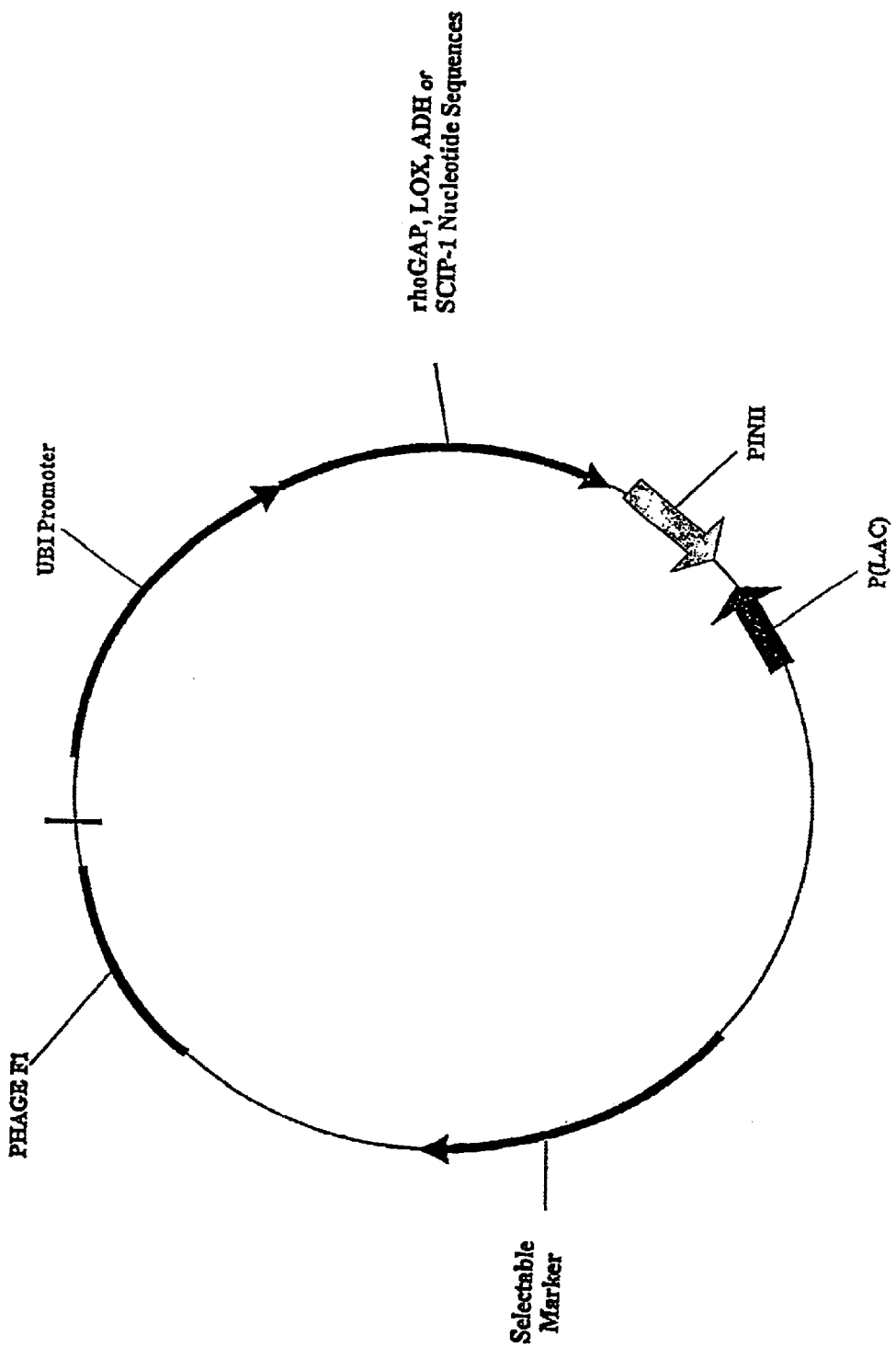
FIG. 1 schematically illustrates an expression vector containing the ubiquitin promoter operably linked the rhoGAP, LOX, ADH, and SCIP-1 nucleotide sequences.

The present invention provides, inter alia, compositions and methods for modulating the total level of proteins of the present invention and/or altering their ratios in a plant. By "modulation" is intended an increase or a decrease in a particular character, quality, substance, or response.

The compositions comprise sunflower nucleic acid and amino acid sequences. Particularly, the nucleotide and amino acid sequence for a sunflower rhoGAP (SEQ ID NOS: 1 and 2), LOX (SEQ ID NOS: 3 and 4), ADH (SEQ ID NOS: 6 and 7) and SCIP-1 (SEQ ID NOS: 8 and 9) are provided. As discussed in more detail below, the sequences of the invention are involved in many basic biochemical pathways that regulate plant growth, development, and pathogen resistance. Methods are provided for the expression of these sequences in a host plant to modulate plant development, developmental pathways, and defense responses. The method involves stably transforming a plant with a nucleotide sequence capable of modulating the plant pathogen defense system operably linked with a promoter capable of driving expression of the nucleotide sequence in a plant cell.

Also provided are LOX and SCIP-1 promoter sequences set forth in SEQ ID NO: 5 and SEQ ID NO: 10, respectively. Methods are provided for the regulated expression of a nucleotide sequence of interest that is operably linked to the LOX or SCIP-1 promoter sequences disclosed herein. Nucleotide sequences operably linked to the LOX or SCIP-1 promoters are transformed into a plant cell. Exposure of the transformed plant to a stimulus, induces transcriptional activation of the nucleotide sequences operably linked to the LOX or SCIP-1 promoters.

rhoGTPase-activating Protein (rhoGAP)

A nucleic acid sequence encoding a rhoGAP polypeptide from sunflower is provided. The rhoGAP sequence shares homology to the conserved rhoGAP genes from humans. The sunflower rhoGAP amino acid sequence shares about 40% homology with the human p50rhoGAP sequence and about 80% homology with an Arabidopsis hypothetical 23.6 kDa protein.

RhoGAPs are a central part of an evolutionarily conserved regulatory system that are involved in cell growth and differentiation. Thus the sequence of the invention finds use in controlling or modulating cell division, differentiation, development, as well as the defense response. Transformed plants can be obtained having altered metabolic states with respect to cell division and cellular processes as well as development and defense response; hence, the methods and compositions may find uses in affecting or studying differentiation.

RhoGAP proteins have been shown to interact with rho members of the ras superfamily. Ras oncogenes were initially found to play an important role in human cancers and have since been shown to play important roles in regulation of cell growth and differentiation. Further, the rhoGAP proteins affect the activity of rhoGTPases (also called rho proteins), which act as molecular switches to regulate affected processes. The rho family of "G proteins" have a GTP-bound form and a GDP-bound form; the relative amount of the GDP-bound form is increased by GTPase activating proteins, or GAPs, which stimulate the intrinsic GTPase activity of the rho proteins.

Processes affected by GAPs include the transduction of hormone signals across cell plasma membranes and the regulation of intracellular transport pathways. For example, rhoGTP-binding proteins have been shown to control signal transduction pathways connecting the activation of actin polymerization to activation of cellular growth factor receptors. Hence, the compositions and methods of the invention find use in the activation or modulation of the cellular actin cytoskeleton. Although there is a great deal of conservation among members of the rhoGAP family, there are a large number of different proteins that contain the rhoGAP domain, and many of these proteins are large and multifunctional. Thus, the rhoGAP genes and/or proteins may contain different elements or motifs or sequence patterns that modulate or affect the activity, subcellular localization, and/or target of the rhoGAP protein. Such elements, motifs, or sequence patterns may be useful in engineering novel enzymes for reducing or enhancing gene expression in particular tissues.

RhoGAP proteins activate rho genes and the related rac genes, which both stimulate actin polymerization. The rho proteins in mammalian systems have been shown to regulate the formation of multi-molecular complexes that are associated with polymerized actin located at the plasma membrane of the cell. Such complexes include actin stress fibers and focal adhesions in fibroblasts as well as the actin-driven phenomenon called membrane ruffling, which is exhibited by many cell types in response to extracellular stimuli. Rho proteins have also been shown to play roles in epithelial cell migration in response to wounding. Expression of the sequences of the invention can be used to modulate or regulate the expression of corresponding GTP-binding proteins, i.e., rho, rac, etc. Hence, the compositions and methods of the invention find use in the activation or modulation of the cellular actin cytoskeleton and other actin-based structures and actin-related processes.

The RhoGAP gene of the present invention additionally finds use in enhancing the plant pathogen defense system. Early plant-cell defense responses include the rearrangement of the cellular actin cytoskeleton to protect the cell from attack. RhoGAP genes are involved in cellular signaling cascades such as the oxidative burst that comprises part of the early defense response in plants. Hence, the compositions and methods of the invention can be used for enhancing resistance to plant pathogens including fungal pathogens, plant viruses, and the like.

Lipoxygenase

A nucleic acid sequence encoding a LOX polypeptide from sunflower is also provided. The sunflower LOX polypeptide shares homology with other known LOX proteins from potato, tomato, cowpea, Arabidopsis, and rice.

The LOX protein has been implicated in a number of important plant developmental processes. LOX catalyzes the hydroperoxidation of polyunsaturated fatty acids containing cis, cis-1,4-pentadiene-conjugated double-bonds. The primary products of LOX-catalyzed reactions are fatty acid hydroperoxides, which are typically metabolized into molecules with known or suspected regulatory activity. For example, LOX derived fatty acid hydroperoxides are precursors to traumatin and jasmonic acid. Traumatin induces cell division and may be involved in the plant wounding response (Zimmerman et al. (1979) *Plant Physiol.* 63:536–541). Jasmonates have been implicated as signal transduction molecules in the response of plants to stress, particularly wounding and pathogen attack (Farner et al. (1992) *Cell* 4:129–134). Therefore, the sunflower LOX gene may play an important role in cell division and defense signal transduction pathways that are regulated by the biosynthesis of traumatin and jasmonic acid.

The LOX gene has also been implicated in the regulation of coordinated gene activation in response to wounding. It is speculated that resistance to pathogen attack is the result of the coordinated accumulation of secondary metabolites and protein products. Some of these products, such as proteinase inhibitors, may directly interfere with digestibility of the injected tissue whereas others products may affect food intake. A potato LOX gene, 13-LOX, has been shown to control the expression levels of proteinase inhibitors in a wounding response to insect feeding (Royo et al. (1999) *Proc. Natl. Acad. Sci. USA* 96:1146–1151). Therefore, the LOX sequences of the present invention may find use in an antifeedant stragedy by regulating proteinase inhibitor levels in plants, and thereby controlling insect and nematode pathogens.

Additionally, LOX-derived fatty acid hydroperoxides and free radical species are cytotoxic and are capable of damaging membranes, proteins, and DNA (Hildebrand et al. (1998) *Curr. Top. Plant Biochem. Physiol.* 7:201–219). Therefore, LOXs may play a role in membrane degradation observed during senescence, wounding, and the hypersensitive response to pathogen attack.

LOX proteins may also play an important role in plant growth and development. There is a positive correlation between LOX activity levels within an organ and its rate of elongation. The concomitant increase in LOXs and the enzymes involved in the metabolism of LOX-derived fatty hydroperoxides is consistent with a role for LOX in generating lipid-derived growth regulators.

Furthermore, in plants, the LOX proteins may be involved in lipid turnover and fat mobilization. Hence, the compositions and methods of the invention find use the turnover of lipids in the developing seedling.

Hence, the LOX sequences of the present invention may be used to modulate many important developmental processes, such as, cell division, seed germination, plant growth and senescence, and/or to enhanced plant resistance to environmental stresses, such as, wounding and pathogen attacks.

The present invention also provides the nucleotide sequences of the LOX promoter. The promoter sequence contains cis-elements that resemble W-boxes, TTGACC (nucleotides 322–327 of SEQ ID NO: 5), and G-boxes, CACGTG (nucleotides 722–727 of SEQ ID NO: 5).

G-box and G-box like sequences are involved in the regulation of a variety of unrelated genes and activate transcription in response to various stimuli including. exposure to visible and UV light (Chattopadhyay et al. (1998) *Plant Cell* 10:673–683), dehydration-stress (Lam el al. (1991) *J Biol Chem* 266: 17131–17135 and Dolferus et al. (1994) *Plant Physiol* 105; 1075–1087), cold stress (Dolferus et a. (1994) *Plant Physiol* 105: 1075–1087), abscisic acid (Narcotte el al. (1989) *Plant Cell* 1: 969–976), sucrose (Urwin et al. (1997) *Plant Mol Biol* 35:929–942), and plant pathogen defense response (Wolfgang el al. (1997) *EMBO Journal* 16:726–738). In addition, G-box-like sequences were also found to determine tissue-preferred expression patterns (Salinas et al. (1992) *Plant Cell* 4: 1485–1493 and Thomas (1993) *Plant Cell* 5: 1401–1410). Functional analysis of G-box containing promoters has shown that the nucleotide sequences immediately flanking the G-box and/or additional cis-acting promoter elements are often required for the G-box to influence transcription activation.

The W-box promoter elements are involved in elicitor-induced gene expression. W-boxes have been identified in a several plant promoters including, for example, members of the WRKY family (Eulgem et al. (1999) *EMBO J.* 18:4689–4699) and members of the pathogenesis-related protein family (Rushton et al. (1996) *EMBO J.* 15:5690–5700). The fungal elicitor responsiveness of these genes is mediated mainly by the presence of the W-boxes in the promoter elements.

Hence, the LOX promoter sequences find use in the regulated expression of an operably linked heterologous gene of interest. More specifically, the nucleotide sequence may find use as an inducible promoter, more specifically, a pathogen-inducible promoter.

Alcohol Dehydrogenase

A nucleic acid sequence encoding an ADH protein from sunflower is also provided. Sequences of the sunflower alcohol dehydrogenase protein (ADH) share about 85–95% sequence homology with plant alcohol dehydrogenases from garden lettuce, potato, tomato, apple, and maize. ADH is an important enzyme in anaerobic metabolism, and it is usually encoded by a small multigene family in flowering plants. In both maize and Arabidopsis, the gene is expressed in seeds, roots, and pollen grains, whereas green aerial plant parts are devoid of detectable ADH activity.

ADH has been implicated in responses to a number of environmental stresses, including low oxygen, drought, salinity, cold acclimation, freezing tolerance, flooding, and wounding. See, for example, Zeevaart et al. (1988) *Annu. Rev. Plant Physiol. Plant Mol. Biol.* 39:439–473; Sanchez et al. (1991) *Abscisic Acid, Physiology and Biochemistry,* Bio Scientific Publishers, Oxford, UK, pp. 210-216; and Bruxelles et al. (1996) *Plant Physiol.* 111:381–391. The ADH sequence of the present invention may find use in modulating a plant's response to adverse environmental stresses.

The sunflower ADH sequences may also find use in modulating the developmental process of fruit ripening. ADH reduces aldehydes to alcohols. Modulation of ADH levels in ripening fruit has been shown to influence the balance between some of the aldehydes and the corresponding alcohols associated with flavor production. Hence, the compositions and methods of the present invention may find use in the modulation of ADH protein levels leading to a more intense "rpe fruit" flavor. See, for example, Speirs et al. (1998) *Plant Physiol.* 11 7:1047–1058.

The ADH sequences of the invention may additionally find use in enhancing plants defense response. Under low oxygen conditions, i.e., a hypotic state, ADH plays a crucial role in cell survival. ADH serves as the major terminal dehydrogenase in regenerating oxidizing power in mature roots, thereby allowing glycolysis to continue in the absence of oxygen. Treatment of a plant with an elicitor increases the levels of active oxygen species in the plant cells and leads to a transient state of oxidative stress. See, for example, Robertson et al. (1995) *Plant Molecular Biology* 27:59–67. Since aerobic respiration is compromised as a result of elicitor action, the ADH sequences of the present invention may find use in modulating a plant's defense against pathogens.

Sclerotinia-inducible Protein-1(SCIP-1)

The nucleic acid sequence encoding a novel sunflower protein, designated Sclerotinia-Inducible Protein-1, SCIP-1, is also provided. SCIP-1 has limited homology with hypothetical proteins from several bacteria.

Transcript levels of SCIP-1 increase in both lesion mimic transgenic plants and Sclerotinia-infected plants. The accumulation of SCIP-1 in lesion mimic and infected sunflower plants implicates that the protein is involved in the plant defense response to Sclerotinia and other pathogens. Hence, the compositions and methods of the invention may find uses for enhancing resistance to plant pathogens, including fungal pathogens, plant viruses, and the like.

Furthermore, a PSI-Blast search revealed that the SCIP-1 sequence of the invention fall into a class of flowering-related plant proteins (CEN and others), as well as some phosphatidylethanolamine-binding proteins (PEBP). The CEN-related proteins are known to be related to a class of phosphatidylethanolamine-binding proteins (PEBP). Banfield et al. ((2000) *J Mol Biol* 297:1159–70) determined the crystal structure of the centroradialis protein from Anthirrhinum. The structure confirmed what had been suspected by sequence homology studies: that the CEN plant proteins are a subset of the family of PEBPs. Mamnialian forms of PEBP are involved in inhibition of MAP kinase signaling, which is a central signaling cascade regulating cell differentiation (Banfield et al. (2000) *J Mol Biol* 297:1159–70). The structure of these proteins suggests that they may play a role in membrane signal transduction (Banfield et al. (1998) *Structure* 6:1245–54). In addition, another recent study (Kuramitsu et al. (2000) *Electrophoresis* 21:660–4) showed that a line of mammalian cells resistant to tumor necrosis factor-alpha contained elevated levels of a protein identified as a PEBP. The report suggested that this PEBP could be responsible for the resistance of certain cell lines to tumor necrosis factor induced cell death. Hence, the SCIP-1 polypeptide of the invention may play a role in signaling, membrane transduction, or in the regulation of cell death.

Furthermore, flowering plants exhibit two types of inflorescence architecture: determinate and indeterminate. The centroradialis mutation causes the normally indeterminate inflorescence of Antirrhinum to terminate in a flower. CEN-related protein have therefore been shown to influence maintenance of the indeterminate state of inflorescence meristems (Pnueli et al. (1998) *Development* 125:1979–1989; Bradley el al. (1996) *Nature* 379:791–7; Bradley-Desmond et al. (1997) *Science* 275:80–83; and Amaya et al. (1999) *Plant Cell* 11:1405–1417). In addition, the SCIP-1 shares homology to Terminal Flower 1 (TFL1) from both *Arabidopsis thaliana* and Brassica. TFL1 has also been shown to influence inflorescence meristem identity. See, for example, Mimida-Naozumi et al. (1999) *Plant-Science* 142: 155–162 and Ohshima et al (1997) *Mol Gen Genet* 254:186–94. Hence, the SCIP-1 sequences of the invention find use in influencing the state of inflorescence of meristem development.

The present invention also provides the nucleotide sequences of the SCIP-1 promoter. The promoter sequence contains cis-elements that resemble W-boxes, GTCAA (nucleotides 364–368 and 371–375 of SEQ ID NOS: 8 and 10), and G-boxes, CACGTG (nucleotides 415–420 of SEQ ID NOS: 8 and 10). As with the LOX promoter sequences, the SCIP-1 promoter sequences may find use in the regulated expression of an operably linked heterologous gene of interest. More specifically, the nucleotide sequence may find use as an inducible promoter, more specifically, a pathogen-inducible promoter.

Compositions

Compositions of the invention include the polynucleotide sequences of the sunflower rhoGAP, LOX ADH, and SCIP-1 genes. In addition, the LOX and SCIP-1 promoter nucleotide sequences are also provided. The polypeptides encoded by those sequences may be involved in various plant developmental processes, including the plant pathogen defense response.

In particular, the present invention provides for isolated nucleic acid molecules comprising nucleotide sequences encoding the amino acid sequences shown in SEQ ID NOS: 2, 4, 7, and 9 or the nucleotide sequences encoding the DNA sequences deposited in a bacterial host as Patent Deposit Nos. PTA-284 and PTA-285 (DNA sequences corresponding to rhoGAP), PTA-286 (DNA sequences corresponding to ADH), PTA-287 (DNA sequences corresponding to LOX), PTA-288 (DNA sequences corresponding to SCIP-1), or the DNA sequences obtained from the overlapping clones deposited in a bacterial host as Patent Deposit Nos. PTA-284 and PTA-285. Further provided are polypeptides having an amino acid sequence encoded by a nucleic acid molecule described herein, for example those set forth in SEQ ID NOS: 1, 3, 6, and 8 or those deposited in a bacterial host as Patent Deposit Nos. PTA-284, PTA-285, PTA-286, PTA-287, PTA-288 and fragments and variants thereof.

The present invention further provides for isolated nucleic acid molecules comprising nucleotide sequences shown in SEQ ID NO: 5 and SEQ ID NO: 10, or nucleotide sequences encoding the DNA sequences deposited in a bacterial host as Patent Deposit Nos. PTA-559 and PTA-1721, and fragments and variants thereof.

By "DNA sequences obtained from the overlapping clones" is intended that the complete DNA sequence of the rhoGAP sequence of the invention (SEQ ID NO: 1) can be obtained by sequencing the two individual clones that together comprise the entire rhoGAP sequence.

Plasmids containing the nucleotide sequences of the invention were deposited with the Patent Depository of the American Type Culture Collection (ATCC), 10801 University Drive, Manassas, Va., 20110-2209 and assigned Accession Nos. PTA-284, PTA-285, PTA-286, PTA-287, PTA-288. and PTA-559. Two of these plasmids, designated PHP15631 (Accession No. PTA-284) and PHP15632 (Accession No. PTA-285) contained overlapping clones. PHP15631 and PHP15632 comprises the 5' and the 3'end of the rhoGAP sequence, respectively. It is noted however, that clones PHP15631 and PHP15632 contain common sequences at the regions where they overlap. One of skill in the art by sequencing the clones and aligning the overlap may obtain the entire sequence of the sunflower rhoGAP. These deposits will be maintained under the terms or the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect development, developmental pathways, and defense response by retaining rhoGAP-, LOX-, ADH-, or SCIP-1-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a rhoGAP nucleotide sequence that encodes a biologically active portion of a rhoGAP protein of the invention will encode at least 12, 25, 30, 50, 100, 150, or 200 contiguous amino acids, or up to the total number of amino acids present in a full-length rhoGAP protein of the invention (for example, 201 amino acids for SEQ ID NO: 2).

A fragment of a LOX nucleotide sequence that encodes a biologically active portion of a LOX protein of the invention will encode at least 22, 30, 50, 100, 150, 200, 300, 400, 500, 600, 700, 800, 900 contiguous amino acids, or up to the total number of amino acids present in a full-length LOX protein of the invention (for example, 901 amino acids for SEQ ID NO: 3).

A fragment of an ADH nucleotide sequence that encodes a biologically active portion of an ADH protein of the invention will encode at least 92, 100, 150, 200, 250, 300, 350, 400 contiguous amino acids, or up to the total number of amino acids present in a full-length ADH protein of the invention (for example, 381 amino acids for SEQ ID NO: 7).

A fragment of a SCIP-1 nucleotide sequence that encodes a biologically active portion of a SCIP-1 protein of the invention will encode at least 8, 15, 25, 30, 50, 100, or 150 contiguous amino acids, or up to the total number of amino acids present in a full-length SCIP-1 protein of the invention (for example, 168 amino acids for SEQ ID NO: 9).

Fragments of a rhoGAP, LOX, ADH, and SCIP-1 nucleotide sequence that are useful as hybridization probes or PCR primers generally need not encode a biologically active portion of a rhoGAP, LOX, ADH, or SCIP-1 protein. Thus, a fragment of a rhoGAP, LOX, ADH, or SCIP-1 nucleotide sequence may encode a biologically active portion of a rhoGAP, LOX, ADH, or SCIP-1 protein, or it may be a fragment that can be used as a hybridization probe or PCR primer using methods disclosed below. A biologically active portion of a rhoGAP, LOX, ADH, or SCIP-1 protein can be prepared by isolating a portion of one of the rhoGAP, LOX, ADH, or SCIP-1 nucleotide sequences of the invention, expressing the encoded portion of the rhoGAP, LOX, ADH, or SCIP-1 protein (e.g., by recombinant expression in vitro), and assessing the activity of the encoded portion of the rhoGAP, LOX, ADH, or SCIP-1 protein. Nucleic acid molecules that are fragments of a rhoGAP, LOX, ADH, SCIP-1 nucleotide sequence comprise at least 16, 20, 50, 75, 100, 150, 200, 250, 300, 350, 400, 450, 500, 550, 600, 650, 700, or 800 nucleotides, or up to the number of nucleotides present in a full-length rhoGAP, LOX, ADH, or SCIP-1 nucleotide sequence disclosed herein (for example, 824 nucleotides for SEQ ID NO: 1, 3806 nucleotides for SEQ ID NO: 3, 1403 nucleotides for SEQ ID NO: 6, and 746 nucleotide sequences for SEQ ID NO: 8).

By "variants" is intended substantially similar sequences. For nucleotide sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a rhoGAP, LOX, ADH, or SCIP-1 protein of the invention. Generally, variants of a particular nucleotide sequence of the invention will have at least 40%, 50%, 60%, 70%, generally at least 75%, 80%, 85%, preferably about 90%, 91%, 92%, 93%, 94%, 95%, 960%, 97%, and more preferably about 98%, 99%, or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, hence they will continue to possess rhoGAP, LOX, ADH, or SCIP-1 activity. Such variants may result from, for example, genetic polymorphism or from human manipulation. Biologically active variants of a native rhoGAP, LOX, ADH, or SCIP-1 protein of the invention will have at least 40%, 50%, 60%, 70%, generally at least 75%, 80%, 85%, preferably about 90%, 91%, 92%, 93%, 94%, 95%, 96%, 97%, 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

Biological activity of the rhoGAP, LOX, ADH and SCIP-1 polypeptides can be assayed by any method known in the art. Assays to measure the developmental pathways and defense responses that are influenced by the rhoGAP, LOX, ADH and SCIP-1 polypeptides having rhoGAP-, LOX-, ADH-, and SCIP-1-like activity are well known in the art. Furthermore, assays to detect rhoGAP-like activity include GTP binding assays (Borg et al. (1994) *Plant Mol. Biol.* 27:175–187); interactions with Rac or Ras (Dielonan et al. (1995) *EMBO J.* 14:5297–5305 and Van Aelst et al. (1996) *EMBO J.* 15:3778–3786); and GTPase and GTPase activating activity assays (Borg et al (1999) *FEBS Letters* 453:341–345). Assays to detect LOX-like activity include, for example, assays to measure LOX enzymatic activity (Maach et al. (1997) *Plant Physiol.* 114:1561–1566, Royo et al. (1 996) *J. Biol. Chem.* 35:21012–21019 and Voros et al. (1998) *FEBS Letters* 251:36–44). Assays to detect ADH-like activity include, for example, ADH enzymatic activity assays (Torres et al. (1976) *Biochem. Genetics* 14:87–97).

The proteins of the invention may be altered in various ways including amino acid substitutions, deletions, truncations, and insertions. Methods for such manipulations are generally known in the art. For example, amino acid sequence variants of the rhoGAP, LOX, ADH, or SCIP-1 proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel el al. (1987) *Methods in Enzymol* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired rhoGAP-, LOX-, ADH-, or SCIP-1-like activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by either an enhanced resistance to pathogens or a modulation in a plant developmental process when expression of the protein sequence is altered.

Variant nucleotide sequences and proteins also encompass sequences and proteins derived from a mutagenic and recombinogenic procedure such as DNA shuffling. With such a procedure, one or more different rhoGAP, LOX, ADH, or SCIP-1 coding sequences can be manipulated to create a new rhoGAP, LOX, ADH, or SCIP-1 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the rhoGAP, LOX, ADH, or SCIP-1 gene of the invention and other known rhoGAP, LOX, ADH, or SCIP-1 genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et at. (1997) *Nature Biotech.* 15:436–438; Moore et al. (1997) *J. Mol. Biol.* 272–336347; Zhang et al (1997) *Proc. Nail. Acad. Sci. USA* 94:450–44509; Crameri et al. (1998) *Nature* 391:288–291; and U.S. Pat. Nos. 5,605,793 and 5,837,458.

The compositions of the invention also include isolated nucleic acid molecules comprising the promoter nucleotide sequences set forth in SEQ ID NO: 5 and SEQ ID NO: 10. By "promoter" is intended a regulatory region of DNA usually comprising a TATA box (nucleotides 808–901 of SEQ ID NO: 5) capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. Such elements include a W-box (nucleotide sequence 322–327 of SEQ ID NO: 5; nucleotide sequence 364–368 and 371–375 of SEQ ID NO: 10) and a G-box (nucleotide sequence 722–727 of SEQ ID NO: 5; nucleotide sequence 415–420 of SEQ ID NO: 10). The promoter sequences of the present invention "regulate" (i.e., repress or activate) transcription from the promoter region. The regulation of transcription by the promoter sequences of the present invention is defined herein as "inducible." By "inducible" is intended the ability of the promoter sequences to regulate expression of an operably linked nucleotide sequence in response to a stimulus.

It is recognized that having identified the nucleotide sequences for the promoter regions disclosed herein, it is within the state of the art to isolate and identify additional regulatory element in the 5' untranslated region upstream from the particular promoter regions defined herein. Thus for example, the promoter regions disclosed herein may further comprise upstream regulatory elements that confer tissue-preferred expression of heterologous nucleotide sequences operably linked to the disclosed promoter sequence. See particularly, Australian Paten No. AU-A-77751/94 and U.S. Pat. Nos. 5,466,785 and 5,635,618.

Fragments and variants of the disclosed LOX and SCIP-1 promoter nucleotide sequences are also encompassed by the present invention. By "fragment" is intended a portion of the nucleotide sequence. Fragments of a nucleotide sequence may retain biological activity and hence retain their transcriptional regulatory activity. Thus, for example, less than the entire promoter sequence disclosed herein may be utilized to drive expression of an operably linked nucleotide sequence of interest, such as a nucleotide sequence encoding a heterologous protein. Alternatively, a fragment of promoter sequence may retain the ability to regulate transcription in the presence of a stimulus when operably linked to a heterologous transcriptional initiation region. Alternatively, fragments of a nucleotide sequence that are useful as hybridization probes generally do not retain biological activity. Thus, fragments of a nucleotide sequence may range from at least about 20 nucleotides, about 50 nucleotides, about 100 nucleotides, and up to the full-length nucleotide sequence of the invention.

Thus, a fragment of a LOX or SCIP-1 promoter nucleotide sequence may encode a biologically active portion of the LOX or SCIP-1 promoter, or it may be a fragment that can be used as a hybridization probe or PCR primer using methods disclosed below. A biologically active portion of a LOX or SCIP-1 promoter can be prepared by isolating a portion of one of the LOX or SCIP-1 promoter nucleotide sequences of the invention, and assessing the activity of the portion of the LOX or SCIP-1 promoter. Nucleic acid molecules that are fragments of a LOX or SCIP-1 promoter nucleotide sequence comprise at least 16, 20, 50, 75, 100, 150, 200, 250, 300, 350, 400, 450, 500, 550, 600, 650, 700, or 800 nucleotides, or up to the number of nucleotides present in a full-length LOX or SCIP-1 promoter nucleotide sequence disclosed herein (for example, 880 nucleotide for SEQ ID NO: 5; 510 nucleotide for SEQ ID NO: 10). Assays to determine the activity of a promoter sequence are well known in the art. For example, a LOX or SCIP-1 promoter fragment or variant may be operably linked to the nucleotide sequence encoding any reporter protein, such as the β-glucosidase protein (GUS reporter) or the luciferase protein. The DNA construct is inserted into the genome of a plant or plant cell and the mRNA or protein level of the reporter sequence is determined. See, for example, Eulgem et al. (1999) *EMBO.* 18: 4689–4699.

Thus, isolated sequences that have promoter activity and which hybridize under stringent conditions to the LOX and SCIP-1 sequences disclosed herein, or to fragments thereof, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99% homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, more sequence identity.

By "variants" of the promoter sequences is intended substantially similar sequences. For nucleotide sequences naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site directed mutagenesis. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire disease resistant sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1 990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}p$, or any other detectable marker. Thus, for example, probes for hybridization can be made by labeling synthetic oligonucleotides based on the disease resistant sequences of the invention. Methods for preparation of probes for hybridization and for construction of cDNA and genomic libraries are generally known in the art and are disclosed in Sambrook el al. (1989) *Molecular Cloning: A Laboratory Manual* (2d ed., Cold Spring Harbor Laboratory Press, Plainview, N.Y.).

For example, an entire sequence disclosed herein, or one or more portions thereof, may be used as a probe capable of specifically hybridizing to the corresponding LOX, SCIP-1, rhoGAP, or ADH sequences and messenger RNAs. To achieve specific hybridization under a variety of conditions, such probes include sequences that are unique among disease resistant sequences and are preferably at least about 10 nucleotides in length, and most preferably at least about 20 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraies (either plaques or colonies; see, for example, Sambrook el at. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C. +16.6(log M)+0.41(% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, New York); and Ausubel et al., eds. (1995)*Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that have promotor activity or encode a rhoGAP, LOX, ADH or SCIP-1 polypeptide and which hybridize under stringent conditions to the rhoGAP, LOX, ADH or SCIP-1 sequences disclosed herein, or to fragments thereof, are encompassed by the present invention. Such sequences will be at least 40% to 50% homologous, about 60%, 65%, or 70% homologous, and even at least about 75% homologous, and even about 80%, 85%, 90%, 91%, 92%, 93%, 94%, 95%, 96%, 97%, 98%, 99% homologous or more with the disclosed sequences. That is, the sequence identity of the sequences may range, sharing at least 40% to 50%, about 60%, 65%, or 70%, and even about 75%, 80%, 85%, 90%, 91%, 92%, 93%, 94%, 95%, 96%, 97% 98%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Nail. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA b* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, Cs BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul el al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments. Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff(1989) *Proc. Natl. Acad. Sci. USA* 89:10915).

For purposes of the present invention, comparison of nucleotide or protein sequences for determination of percent sequence identity to the rhoGAP, LOX, ADH, and SCIP-1 sequences disclosed herein is preferably made using the ClustalW program (Version 1.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point $(T_m)$ for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Disease and Pests

Compositions and methods for controlling pathogenic agents are provided. The anti-pathogenic compositions comprise sunflower nucleotide and polypeptide sequences. Particularly, the sunflower nucleic acid and amino acid sequences are selected from rhoGAP-1, LOX, ADH, and SCIP-1. Accordingly, the compositions and methods are useful in protecting plants against fungal pathogens, viruses, nematodes, insects and the like.

By "disease resistance" or "pathogen resistance" is intended that the plants avoid the disease symptoms which are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a a, decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et. al. (1992) *J. Biol. Chem.* 267: 2228–2233, both of which are herein incorporated by reference).

Methods for increasing pathogen resistance in a plant are provided. The methods involve stably transforming a plant with a DNA construct comprising an anti-pathogenic nucleotide sequence of the invention operably linked to promoter that drives expression in a plant. Such methods may find use in agriculture particularly in limiting the impact of plant pathogens on crop plants. The anti-pathogenic nucleotide sequences comprise the sunflower rhoGAP, LOX, ADH, or SCIP-1 nucleic acid molecules. While the choice of promoter will depend on the desired timing and location of expression of the anti-pathogenic nucleotide sequences, preferred promoters include constitutive and pathogen-inducible promoters.

Additionally, the compositions can be used in formulation use for their disease resistance activities. The proteins of the invention can be formulated with an acceptable carrier into a pesticidal composition(s) that is for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Additionally, transformed plants, plant cells, plant tissues and seeds thereof are provided.

It is understood in the art that plant DNA viruses and fungal pathogens remodel the control of the host replication and gene expression machinery to accomplish their own replication and effective infection. The present invention may be useful in preventing such corruption of the cell.

As discussed above, the sequences encoding the sunflower rhoGAP, LOX, ADH, and SCIP-1 are involved in many basic biochemical pathways and cellular functions that influence the plant defense response. Hence, the sequences of the invention may find use in disrupting cellular function of plant pathogens or insect pests as well as altering the defense mechanisms of a host plant to enhance resistance to disease or insect pests. While the invention is not bound by any particular mechanism of action, the gene products, probably proteins or polypeptides, function to inhibit or prevent plant diseases in a plant. Such gene products may be anti-pathogenic. It is recognized that the present invention is not dependent upon a particular mechanism of defense. Rather, the genes and methods of the invention work to increase resistance of the plant to pathogens independent of how that resistance is increased or achieved.

The methods of the invention can be used with other methods available in the art for enhancing disease resistance in plants. Similarly, the plant defense mechanisms described herein may be used alone or in combination with other proteins or agents to protect against plant diseases and pathogens. Although any one of a variety of second nucleotide sequences may be utilized, specific embodiments of the invention encompass those second nucleotide sequences that, when expressed in a plant, help to increase the resistance of a plant to pathogens. It is recognized that such second nucleotide sequences may be used in either the sense or antisense orientation depending on the desired outcome. Other plant defense proteins include those described in WO 99/43823 and WO 99/43821, all of which are herein incorporated by reference.

Additionally, the LOX and SCIP-1 promoter nucleotide sequences disclosed herein are also useful for genetic engineering of plants to express a phenotype of interest. The promoter sequences may be used to regulate expression of any heterologous nucleotide sequence. Alternatively, the LOX or SCIP-1 promoter sequence may be used to drive expression of its native, i.e., naturally occurring, LOX or SCIP-1 gene sequence disclosed herein. In a specific embodiment, the LOX or SCIP-1 promoter sequences are operably linked to an anti-pathogenic nucleotide sequence and drive expression of said sequence in a plant cell. The LOX or SCIP-1 promoter sequences may therefore be used in creating or enhancing pathogen or disease resistance in a transformed plant.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* f.sp. *glycinea*, *Macrophomina phaseolina*, *Rhizoctonia solani*, *Sclerolinia sclerotiorum*, *Fusarium oxyspornm*, *Diaporthe phaseolorum* var. *sojae* (*Phomopsis sojae*), *Diaporthephaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Septoria glycines*, *Phyllosticia sojicola*, *Alternaria alternata*, *Pseudomonas syringae* p.v. *glycinea*, *Xanthomonas campestris* p.v. *phaseoli*, *Microsphaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermalum*, *Pythium ultimum*, *Pythium debaryanum*, Tomato spotted wilt virus, *Heterodera glycines Fusarium solani*; Canola: *Albugo candida*, *Alternaria brassicae*, *Leptosphaeria maculans*, *Rhizoctonia solani*, *Sclerotinia scierotiorum*, *Mycosphaerella brassiccola*, *Pythium ultimum*, *Peronospora parasitica*, *Fusarium roseum*, *Alternaria alternata*; Alfalfa: *Clavibater michiganese* subsp. *insidiosum*, *Pythium ultimum*, *Pythium irregulare*, *Pythium splendens*, *Pythium debaryanum*, *Pythium aphanidermatum*, *Phytophihora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium*, *Xanthomonas campestris* p.v. *alfalfae*, *Aphanomyces euteiches*, *Stemphylium herbarum*, *Stemphylium alfalfae*; Wheat: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Cofloteirichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Bome Wheat Mosaic Virus, Wheat Streak Mosaic Virus, Wheat Spindle Streak Virus, American Wheat Striate Virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, High Plains Virus, European wheat striate virus; Sunflower: *Orobanche*, *Plasmophora halstedii*, *Sclerotinia scierotiorunm*, Aster Yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* pv. *carotovora*, *Cephalosponium acremonium*, *Phytophthora cryptogea*, *Albugo tragopogonis*; Corn: *Fusarium moniliforme* var. *subglutinans*, *Erwinia stewartii*, *Fusarium moniliforme*, *Gibberella zeae* (*Fusarium graminearu*), *Slenocarpella maydi* (*Diplodia maydis*), *Pythium irregulare*, *Pythium debaryanum*, *Pythium graminicola*, *Pythium splendens*, *Pythiun ultimum*, *Pythium aphanidermatum*, *Aspergillusflavus*, *Bipolaris maydis* O,T (*Cochliobolus heterostrophus*), *Helminthosporium carbonum* I, II & III (*Cochliobolus carbonum*),*Exserohilum turcicum* I, II & III, *Helminthosporium pedicellatum*, *Physoderma maydis*, *Phyllosticta maydis*, *Kabatiella-maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunala*, *Curvularia inaequalis*, *Curvularia pallescens*, *Clavibacter michiganense* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Erwinia chrysanthemi* pv. *zea*, *Erwinia carotovora*, Corn stunt spiroplasma, *Diplodia macrospora*, *Sclerophthora macrospora*, *Peronoscierospora sorghi*, *Peronosclerospora philippinensis*, *Peronoscierospora maydis*, *Peronoscierospora sacchari*, *Sphacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum nurcicum*, *Colletotrichum graminicola* (*Glomerella graminicola*), *Cercospora sorghi*, *Gloeocercospora sorghi*, *Ascochyta sorghina*, *Pseudomonas synngae* p.v. *syringae*, *Xanthomonas campestris* p.v. *holcicola*, *Pseudomonas andropogonis*, *Puccinia purpurea*, *Macrophomina phaseolina*, *Perconia circinata*, *Fusarium monilforme*, *Alternaria alternata*, *Bipolaris sorghicoia*, *Hefminthosporium sorghicola*, *Curvularia lunata*, *Phoma insidiosa*, *Pseudomonas avenae* (*Pseudomonas alboprecipitans*), *Ramulispora sorghi*, *Ramulispora sorghicola*, *Phyliachara sacchari*, *Sporisorium reilianum* (*Sphacelotheca reiliana*), *Sphacelotheca cruenta*, *Sporisorium sorghi*, Sugarcane mosaic H, Maize Dwarf Mosaic Virus A & B, *Claviceps sorghi*, *Rhizoctonia solani*, *Acremonium strictum*, *Sclerophthona macrospora*, *Peronosclerospora sorghi*, *Peronosclerospora philippinensis*, *Sclerospora graminicola*, *Fusarium graminearum*, *Fusarium oxysporum*, *Pythium arrhenomanes*, *Pythium graminicola*, etc.

Nematodes include parasitic nematodes such as root-knot, cyst, lesion, and renniform nematodes, etc.

Insect pests include insects selected from the orders Coleoptera, Diptera, Hymenoptera, Lepidoptera, Mallophaga, Homoptera, Hemiptera, Orthoptera, Thysanoptera, Derrnaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer, *Agrotis ipsilon*, black cutworm; *Helicoverpa zea*, corn earworm; *Spodoptera frugiperda*, fall armyworm; *Diatraea grandiosella*, southwestern corn borer, *Elasmopalpus lignosellus*, lesser cornstalk borer; *Diatraea saccharalis*, surgarcane borer; *Diabrotica virgifera*, western corn rootworm; *Diabrotica longicornis barberi*, northern com rootworm; *Diabrotica undecimpunciata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum majdis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemyaplatura*, seedcom maggot; *Agromyza parvicornis*, corn blot leafininer, *Anaphothrips obscrurus*, grass thrips; *Solenopsis milesta*, thief ant; *Tetranychus urticae*, twospotted spider mite; Sorghum: *Chilopartellus*, sorghum borer; *Spodoptera frugiperda*, fall arnywormn; *Helicoverpa zea*, corn earworm; Elasmopalpus lignosellus, lesser cornstalk borer; *Feltia subterranea*, granulate cutworm; *Phyllophaga crinita*, white grub; Eleodes, Conoderus, and Aeolus spp,, wireworms; *Oulema melanopus*, cereal leaf beetle; *Chaetocnema pulicaria*, corn flea beetle; *Sphenophorus maidis*, maize bilibug; *Rhopalosiphum maidis*; com leaf aphid; *Siphaflava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctat*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctala*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentiazis*, differential grasshopper; *Melanoplus sanguinipes*, migratory grasshopper; *Mayetiola daestructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exciamationis*, sunflower beetle; *Bothyrus gibbosus*, carrot beetle; *Neolasioptera murtfeldtiana*, sunflower seed midge; Cotton: *Heliothis virescens*, cotton budwonm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper, *Melanoplus differentialis*, differential grasshopper; *Thrips tabaci*, onion thrips; *Franklinkiella fusca*, tobacco thrips; *Tetranychus cinnabarinus*, carnine spider mite; *Tetranychus urticae*, twospotted spider mite; Rice: *Diatraea saccharalis*, sugarcane borer; *Spodoptera fiugiperda*, fall armywonn; *Helicoverpa zea*, corn earworm; *Colaspis brunnea*, grape colaspis; *Lissorhopirus oryzophilus*, rice water weevil; *Sitophilus oryzae*, rice weevil; *Nephotettix nigropictus*, rice leafhopper; *Blissus leucopterus leucopterus*, chinch bug; Soybean: *Pseudoplusia includens*, soybean looper; *Anticarsia gemmatalis*, velvetbean caterpillar, *Plathypena scabra*, green cloverworm; *Ostrinia nubilalis*, European corn borer, *Agrotis ipsilon*, black cutworm; *Spodoptera exigua*, beet armyworm; *Heliothis virescens*, cotton budworn; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thnips tabaci*, onion thrips; *Tetranychus turkestani*, strawberry spider mite; *Tetranychus urticae*, twospotted spider mite; Barley: *Ostrinia nubilalis*, European corn borer; *Agrotis epsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seelcom maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamesira configurata*, Bertha armyworm; *Plutella xylostella*, Diamond-back moth; Delia ssp., Root maggots.

Expression of Sequences

The nucleic acid sequences of the present invention can be expressed in a host cell such as bacteria, yeast, insect, mammalian, or preferably plant cells. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

By "host cell" is meant a cell, which comprises a heterologous nucleic acid sequence of the invention. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The disease resistant sequences of the invention are provided in expression cassettes or DNA constructs for expression in the plant of interest. The cassette will include 5' and 3' regulatory sequences operably linked to a rhoGAP, LOX, ADH, or SCIP-1 sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the disease resistant sequence to be under the transcriptional regulation of the regulatory regions. The expression cassette may additionally contain selectable marker genes.

The expression cassette will include in the 5'-3' direction of transcription, a transcriptional and translational initiation region, a disease resistant DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of the disease resistant RNA/protein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. lumefaciens*, such as the octopine synthase and nopaline synthase termination regions. See also Guerineau et at. (1991)*Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Dallas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, tie genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); polyvirus leaders, for example, TEV leader (Tobacco Etch Virus) (Allison et a. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate anmmonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad & Sci. USA* 89:6314–6318; Yao et al. (1992) *Cell* 71:63–72; Rezmloff (1992) *Mol. Microbiol.* 6:2419–2422; Baridey et al. (1980) in *The Operon*, pp. 177–220; Hu et al. (1987) *Cell* 48:555–566; Brown el al. (1987) *Cell* 49,603–612; Figge et al. (1988) *Cell* 52:713–722; Deuschle et al. (1989) *Proc. Natl. Acad. Aci.* USA 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hiavka et al. (1985) *Handbook of Experimental Pharmacology*, Vol. 78 ( Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in plants. Such constitutive promoters include, for example, the core promoter of the Rsyn7 (PCT Application Serial No. US99/03863); Scp1 promoter (U.S. patent application Ser. No. 09/028,819), rice actin (McElroy et al. (1990) *Plant Cell* 2:163–171); ubiquitin (Christensen et al. (1989) *Plant Mol. Biol.* 12:619–632 and Christensen et al (1992) *Plant Mol. Biol.* 18:675–689); pEMU (Last et at (1991) *Theor. Appl. Genet.* 81:581–588); MAS (Velten et a. (1984) *EMBO J.* 3:2723–2730); ALS promoter (U.S. application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also the copending application entitled "inducible Maize Promoters", U.S. patent application Ser. No. 09/257,583, filed Feb. 25, 1999.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen Fusarium moniliforme (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); system in (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon di the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

The method of transformation/transfection is not critical to the instant invention; various methods of transformation or transfection are currently available. Thus, any method, which provides for effective transformation/transfection may be employed. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22;421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, *Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those Brassica species useful as sources of seed oil, alfalfa (*Medicago saliva*), rice (*Oryza saliva*), rye (*Secale cereale*), sorghum (*Sorghum bicolor, Sorghum vulgar*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum*

*tuberosum*), peanuts (*Arachis hypogaea*), cotton (*Gossypium barbadense, Gossypium hirsutum*), sweet potato (*Ipomoea batatus*), cassava (*Manihol esculenta*), coffee ( Coffea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g., *Lactuca saliva*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbiapulcherrima*), and chrysanthemum. Conifers that may be employed in practicing the present invention include, for example, pines such as loblolly pine (*Pinus taeda*), slash pine (*Pinus elliolit*), ponderosa pine (*Pinus ponderosa*), lodgepole pine (*Pinus contorta*), and Monterey pine (*Pinus radiata*); Douglas-fir (*Pseudolsuga menziesit*); Western hemlock (*Tsuga canadensis*); Sitka spruce (*Picea glauca*); redwood (*Sequoia semperens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Prokaryotic cells may be used as hosts for expression. Prokaryotes most frequently are represented by various strains of *E. coli;* however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E coli.* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva et al. (1983) *Gene* 22:229–235), Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous nucleotide sequences in yeast is well known (Sherman et al. (1982) *Methods in Yeast Genetics,* Cold Spring Harbor Laboratory). Two widely utilized yeasts for production of eukaryotic proteins are *Saccharomyces cerevisiae* and *Pichia pastoris.* Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider (1987) *J. Embryol. Exp. Morphol.* 27:353–365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VPI intron from SV40 (Sprague et al.(1 983) *J. Virol.* 45:773–78 1). Additionally, gene sequences to control replication in the host cell may be incorporated into the vector such as those found in bovine papilloma virus type-vectors (Saveria-Campo (1985) *DNA Cloning Vol. II a Practical Approach,* D. M. Glover, Ed., IRL Press, Arlington, Va., pp. 213–238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler (1997) *Biochemical Methods in Cell Culture and Virology*, Dowden, Hutchinson and Ross, Inc.).

It is recognized that with these nucleotide sequences, antisense constructions, complementary to at least a portion of the messenger RNA (mRNA) for the disease resistant sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Patent Nos. 5,283,184 and 5,034,323; herein incorporated by reference.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

In some embodiments, the content and/or composition of polypeptides of the present invention in a plant may be modulated by altering, in vivo or in vitro, the promoter of a gene to up- or down- regulate gene expression. In some embodiments, the coding regions of native genes of the present invention can be altered via substitution, addition, insertion, or deletion to decrease activity of the encoded enzyme. See, e.g., Kmniec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development, Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly maize.

Methods of Use for LOX and SCIP-1 Promoter Sequences

The nucleotide sequences for the LOX and SCIP-1 promoters disclosed in the present invention, as well as variants and fragments thereof, are useful in the genetic manipulation of any host cell, preferably plant cell, when assembled with a DNA construct such that the promoter sequence is operably linked to a nucleotide sequence encoding a heterologous protein of interest. In this manner, the nucleotide sequences of the LOX and SCIP-1 promoter of the invention are provided in expression cassettes along with heterologous nucleotide sequences for expression in the host cell of interest.

The promoters for the LOX and SCIP-1 genes may regulate expression of operably linked nucleotide sequences in an inducible manner. That is, expression of the operably linked nucleotide sequences in a host cell (i.e., plant cell) is induced in response to a stimulus. By "stimulus" is intended a chemical, which may be applied externally or may accumulate in response to another external stimulus; a pathogen, which may, for example, induce expression as a result of invading a plant cell; or other factor such as environmental stresses, including but not limited to, drought, temperature, and salinity.

As such, the stimulus either directly or indirectly regulates the activity (i.e., an increase in initiation or expression) of an inducible promoter. By "direct action" is intended that the stimulus regulates transcription via a direct interaction between the stimulus and the DNA sequence. By "indirect action" is meant that the regulation occurs via an interaction between the stimulus and some other endogenous or exogenous component in the system, the ultimate result of the indirect action being regulation of the inducible promoter. The stimulus c result from a biotic or abiotic stress, including for example, tissue wounding (i.e., insect herbivory, wind, intentional abiotic infliction of tissue injury or wounding for the purpose of experimentation and/or expression analysis); wound-responsive chemicals (i.e., chemicals that result in the activation of wound-response response signal transduction pathways, including, various hormones, jasmonic acid, abscissic acid, linolenic acid, ethylene, their chemical analogues, derivatives, precursors, and the like); pathogens (i.e, fungi, bacteria, nematodes, mycoplasmas, viruses, and insects and the like); and various environmental stresses (i.e., heat, drought, cold, reactive oxygen species and/or radiation). Hence, the promoter of the present invention can be used in combination with a nucleotide sequence that enhances disease resistance, and the compositions therefor find use in the defense of a plant against disease, pathogens, and the like.

Synthetic hybrid promoter regions are known in the art. Such regions comprise upstream promoter elements of one nucleotide sequence operably linked to the promoter element of another nucleotide sequence. In an embodiment of the invention, heterologous gene expression is controlled by a synthetic hybrid promoter comprising the LOX or SCIP-1 promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton et al. (1998) Curr. Opin. Plant Biol. 1:311–315. Alternatively, a synthetic LOX or SCIP-1 promoter sequence may comprise duplications of the upstream promoter elements found within the LOX or SCIP-1 promoter sequence. Such elements include, for example the G-box (nucleotides 722–727 of SEQ ID NO: 5; nucleotides 415–420 of SEQ ID NO: 10) or W-box (nucleotides 322–327 of SEQ ID NO: 5; nucleotides 364–368 and 371–375 of SEQ ID NO. 10).

It is recognized that the promoter sequence of the invention may be used with its native LOX or SCIP-1 coding sequences. A DNA construct comprising the LOX or SCIP-1 promoter operably linked with its native LOX or SCIP-1 gene may be used to transform any plant of interest to bring about a desired phenotypic change, such as enhanced disease resistance. Where the promoter and its native gene is naturally occurring within the plant, ie., in sunflower, transformation of the plant with these operably linked sequences also results in either a change in phenotype, such as enhanced disease resistance, the insertion of operably linked sequences within a different region of the chromosome thereby altering the plant's genome, or the modulation in the level of expression of the nucleotide sequence of interest.

In another embodiment of the invention, expression cassettes will comprise a transcriptional initiation region comprising the LOX or SCIP-1 promoter nucleotide sequences disclosed herein, or variants or fragments thereof, operably linked to the heterologous nucleotide sequence whose expression is to be controlled by the inducible promoter of the invention.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997; U.S. Pat. Nos. 5,703,049, 5,885,801, and 5,885,802; herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) Eur. J. Biochem. 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and PCT/US97/20441, filed Oct. 31, 1997, the disclosures of which are herein incorporated by reference. Other proteins include methionine-rich plant proteins such as from sunflower seed (Lilley et al. (1989) Proceedings of the World Congress on Vegetable Protein Utilization in Human Foods and Animal Feedstuffs, ed. Applewhite (American Oil Chemists Society, Champaign, Ill.), pp. 497–502; herein incorporated by reference); corn (Pedersen et al. (1986) J. Biol. Chem. 261:6279; Kirihara et al. (1988) Gene 71:359; both of which are herein incorporated by reference); and rice (Musumura et al. (1989) Plant Mol. Biol. 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, Bacillus thuringiensis toxic protein genes (U.S. Pat. Nos. 5,366,892; 5,747,450; 5,736,514; 5,723,756; 5,593,881; and Geiser et al. (1986) Gene 48:109); lectins (Van Damme et al. (1994) Plant Mol. Biol. 24:825); and the like.

Genes encoding disease resistance traits include detoxification genes, such as against fuimonosin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like.

Herbicide resistance traits may include genes coding for resistance to herbicides that act to inhibit the action of acetolactate synthase (ALS), in particular the sulfonylureatype herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins, described in U.S. application Ser. No. 08/838,763 (filed Apr.10, 1997) and U.S. Pat. Nos. 5,703,049, 5,885,801, and 5,885,802, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Patent No. 5,602,321. Genes such as β-Ketothiolase, PHBase (polyhydroxyburyrate synthase), and acetoacetyl-CoA reductase (see Schubert et al. (1988) *J. Bacteriol.* 170:5837–5847) facilitate expression of polyhyroxyalkanoates (PHAs). Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The following examples are offered by way of illustration and not by way of limitation.

EXPERIMENTAL

Example 1

The Isolation of Sunflower Disease Resistant Genes and the LOX and SCIP-1 Promoter Sequences Materials and Methods Plant Material Sunflower plants were grown in the greenhouse and growth chamber. The sunflower line SMF 3 and oxox-transgenic sunflower were used for an RNA profiling study by CuraGen. Sunflower pathogen, *Sclerotinia sclerotiorum* was maintained on PDA plate at 20° C. in dark.

reparation of Total RNA for RNA Profiling Study and Northern Analysis

Plant materials were ground in liquid nitrogen and total RNA was extracted by the Tri-agent Method. For each RNA profiling study, RNA samples from 6-week-old sunflower leaves and stems of transgenic sunflower plants expressing a wheat oxalate oxidase gene (oxox) were compared with RNA samples from the non-transformed parent sunflower line SMF3. Total RNA (20 ug) was separated in a 1% agarose gel containing formaldehyde. Ethidium bromide was included to verify equal loading of RNA. After transfer onto Hybond N+membrane, the blots were hybridized with $^{32}$P-labelled rhoGAP, LOX, ADH, or SCIP-1 cDNA probes. A duplicate blot was hybridized with a ribosomal 18S RNA probe as a control. Hybridization and washing conditions were performed according to Church and Gilbert.

RNA Profiling

Differences in the expression of specific genes between sunflower plants expressing a wheat oxalate oxidase gene and the sunflower line SMF3 were determined using gene expression profiling. Total RNA was analyzed using the gene expression profiling process (GeneCalling®) as described in U.S. Pat. No. 5,871,697, herein incorporated by reference.

Isolation of Full-Length or Flanking Sequences by PCR Amplification of cDNA Ends The four cDNAs of the present invention were isolated by using RNA profiling and PCR-based technologies. RNA profiling studies were conducted through the collaboration with CuraGen Corp. The sequence information generated by the CuraGen study was used to design gene specific primers to amplifying both 3' and/or 5' end regions of the target genes using PCR-based RACE technology. Sclerotinia-infected and oxox-induced cDNA libraries or cDNAs made by the Marathon cDNA Amplification Kit (Clontech) were used as template for PCR amplification. To facilitate cloning full-length cDNAs from initial cloned regions, a pair of 28 bp vector primers were designed that flanked the cDNAs on both ends (3' and 5') of the pBS vector. Amplification of either the 5' or 3' end of the cDNA was accomplished using a vector primer (pBS-upper or pBS-lower) paired with a gene specific primer. The 5' end of a specific gene with the intact ATG start codon was cloned and sequenced. The full-length cDNA was amplified by using a new gene specific 5' primer containing sequences upstream of the ATG start codon and a 3' primer containing vector sequences.

PCR reactions were performed in a total volume of 25 µl in 10 mM Tris-HCL, pH 8.3; 1.5 mM MgCl$_2$; 50 mM KCl; 0.1 mM dNTPs; 0.25 µM of each primer with 0.5 units of advantage cDNA polymerase mix (Clontech) or Pwo DNA polymerase (Boehringer). Genomic DNA and/or EDNA library mixtures were used as template for PCR amplification.

Isolation of Disease Inducible Promoters

The promoter regions of t he LOX and SCIP-1 genes were isolated from sunflower genomic DNA using Universal Genomic Walker Kit (clontech) according to the manufactures instructions. Restriction digested genomic DNAs were ligated with an adapter to construct pools of genomic DNA fragments for walking by PCR.

Analysis of Amplified PCR Products

Amplified PCR fragments with the e expected sizes were individually sliced out of the gel for second round PCR re-amplification. The second round of PCR was carried out using the same conditions as initial PCR. Each second round PCR product that showed a single band of the expected size was cloned into the TA vector (Clontech) according to the manufacturer's instructions. Positive clones were selected for DNA sequencing using an Applied Biosystems 373A (ABI) automated sequencer at the Nucleic Acid Analysis Facility of Pioneer Hi-Bred Int'l Inc. DNA sequence analysis was carried out with the Sequencer (3.0). Multiple-sequence alignments (Clustal W) of the DNA sequence were carried out with the Curatool (CuraGen).

Construction of the Sclerolinia-infected and Resistance-Enhanced (Oxox-Induced) Sunflower cDNA Libraries Six-week old SMF3 sunflower plants were infected with Sclerotinia Sclerotium by petiole inoculation with Sclerotinia-infected carrot plugs. Six days after infection, leaf and stem tissues were collected from infected plants for total RNA isolation. Total RNA was also isolated from 6-week-old sunflower oxox-transgenic plants (line 610255) expressing a wheat oxalate oxidase gene. Our previous studies have shown that elevated levels of $H_2O_2$, SA, and PR1 protein were detected in oxox-transgenic plants at the 6-week stage and that the plants showed more resistance to Sclerotinia infection. The mRNAs were isolated using a mRNA purification kit (BRL) according to the manufacture's instructions. The cDNA libraries were constructed using the ZAP-cDNA synthesis kit and the pBluescript phagemid (Stratagene). A cDNA library mixture for PCR cloning was made of oxox-transgenic stem and Sclerotinia-infected leaf libraries (1:2 mix).

Fungal Infection and Chemical Treatments

Sunflower plants SMF3 were planted in 4-inch pots and grown in greenhouse for first four weeks. After transfer to growth chamber, plants were maintained under 12-hour photoperiod at 22° C. with an 80% relative humidity. Six-week old plants were inoculated with Sclerotinia-infected carrot plugs or sprayed with four different chemicals at the given concentration. For each plant, tree petioles were inoculated and wrapped with 1×2 inch parafilm. Plant tissue samples were harvested at different time points and immediately frozen in liquid nitrogen and then stored at −80° C.

CuraGen Analysis and Database Search

An RNA profiling study identified 7 bands that were induced in oxox-transgenic and Sclerotinia-infected sunflower plants (Table 1).

logues by blast search of Genbank. The bands were induced 3.37- to 11.82- fold higher in Sclerotinia-infected samples compared with uninfected control samples. The sunflower LOX nucleotide sequence is shown in SEQ ID NO: 3. The LOX ORF extends from nucleotide 881 to nucleotide 3583. The LOX ORF encodes a 901 amino acid protein (SEQ ID NO: 4) with a predicted molecular weight of 101.37 kDa and a pI of 5.61. The sunflower LOX protein shares homology to other LOX genes from potato (Accession No. 034370), tomato (Accession No. Q96573), cowpea (Accession No. P93698), Arabidopsis (Accession No. LOXC_ARATH) and rice (Accession No. LOXC_ORYSA).

The CuraGen band i0a0-289.5 was induced 7.7-fold higher in Sclerotinia-infected samples compared with uninfected control samples. PCR-based cloning of this band allowed the isolation of a cDNA encoding a 381 amino acid polypeptide, which has 85–95% amino acid identity with known plant ADH sequences from garden lettuce (Accession No. Q40249), potato (Accession No. P14674), tomato (Accession No. P28032), apple (Accession No. P48977), and maize (Accession No. P00333).

The CuraGen bands 10m0-273.9 and 10m0-94.2 were induced 23.2- and 12.3- fold higher in Sclerotinia-infected samples compared with uninfected control samples, respectfully. PCR-based cloning of this band allowed two partial cDNA clones to be isolated. The full length cDNA of SCIP-1 encodes a 168 amino acid polypeptide. A BLASTP (version 2.0) sequence alignment showed that SCIP-1 has about 41% identity from amino acid 10–167 with a conserved protein from *Methanobacterium thermoautotrophicum* (Accession No. O26373), about 34% identity from amino acid resi-

TABLE 1

Summary of RNA profiling results from four sets of experiments.

| Gene name | Fold Diff | Band Id | Stem & Leaf Oxox-48d | Leaf Oxox-48d | Leaf Infection | Stem Infection |
| --- | --- | --- | --- | --- | --- | --- |
| GTPase-activating protein (rhoGAP) | +2.6 | m0v0-120.8 | +2.58 | +3.15 | 0 | 0 |
| Lipoxygenase | +11.8 | m1n0-257.6 | 0 | 0 | 0 | +11.82 |
| Lipoxygenase | +6.4 | w0h0-279.1 | 0 | 0 | 0 | +6.42 |
| Lipoxygenase | +3.4 | m0r0-276.7 | 0 | 0 | 0 | +3.37 |
| Alcohol dehydrogenase | +7.7 | i0a0-289.5 | +7.69 | 0 | 0 | +2.21 |
| SCIP-1 | −+3.2 | l0m0-273.9 | 0 | 0 | +23.24 | 0 |
| SCIP-1 | +12.3 | l0m0-94.2 | 0 | +.74 | +12.28 | 0 |

Note: three lipoxygenase bands belong to same isolated sunflower LOX cDNA and the two SCIP-1 bands are the same cDNA.

The CuraGen band mOvO-120.8 was induced 2 to 3 fold in oxox-transgenic plants and showed lesion mimic phenotype (Table 1). The translated product of CuraGen band m0v0-120.8 shares (amino acids 23–118 of SEQ ID NO: 2) 78% amino acid identity with an Arabidopsis hypothetical 23.6 kDa protein (Accession No. 081806). Band m0v0-120.8 represents amino acids 23–118 of SEQ ID NO: 2. The nucleotide sequence encoding the rhoGAP polypeptide is shown in SEQ ID NO: 1. The sunflower rhoGAP clone is 824 bp long with an ORF from nucleotides 35 to nucleotide 637 from the 5' end. It encodes a 201 amino acid protein (SEQ ID NO: 2) with a molecular weight of 23.4 kDa and pI of 8.1. A BLASTX (version 2.0) search indicated that the sunflower rhoGAP-1 protein has sequence homology (about 40%) with human p50rhGAP (Accession No. Z23024) and also shares sequence homology with the *Lotus japonicus* rhoGAP (Accession No. AF064787).

Three of the CuraGen bands (m1 n0-257.6, w0h0-279.1 and m0r0-276.7) were identified as lipoxygenase homodues1–163 with a hypothetical 20.7 kDa protein from *Pyrococcus abyssi* (Accession No. CAB50064), about 35% identity from amino acid residues 13–159 with a conserved hypothetical protein from *Archaeoglobus fulgidus* (Accession No. O28575), about 36% identity with a hypothetical 16.5 kDa protein from *Chlamydia trachomatis* (Accession No. O84741), about 36% identity from amino acid residues 21–163, about 36% identity from amino acid 21 to 163 with a long hypothetical protein from *Pyrococcus horikoshii* (Accession No. O58984), about 35% identity with a hypothetical 18.9 kDa protein from *Aquifex aeolicus* (Accession No. O67293), about 35% identity from amino acid residues 21–167 with a hypothetical 17.1 kDa protein from *E. coli* (Accession No. P12994), and about 35% identity from amino acid residues 8–135 with a hypothetical 19.5 kDa protein from *E. coli* (Accession No. P77368).

As discussed further in example 2, the transcript encoding SCIP-1 was up-regulated in infected tissue as compared to control tissue. The accumulation of SCIP-1 in lesion mimic and infected sunflower plants suggests that the polypeptide may be involved in the plant defense response to Sclerotinia and other pathogens.

Position specific iterative BLAST (PSI-BLAST) (http://www.ncbi.nlm.nih.gov/Education/BLASTinfo/psi 1.htm1) was performed on the SCIP-1 sequence of the invention. PSI-BLAST refers to a feature of BLAST 2.0 in which a profile (or position specific scoring matrix, PSSM) is constructed (automatically) from a multiple alignment of the highest scoring hits in an initial BLAST search. The PSSM is generated by calculating position-specific scores for each position in the alignment. Highly conserved positions receive high scores and weakly conserved positions receive scores near zero. The profile is used to perform a second (BLAST search and the results of each "iteration" used to refine the profile. The second profile is used to perform another BLAST search and so on, until the profile no longer brings back new information and is said to have "converged". This iterative searching strategy results in increased sensitivity. PSI-BLAST searches thus can identify subtle homologies to annotated entries in the database. PSI-BLAST is an important tool for predicting both biochemical activities and function from sequence relationships.

A search was set up using the Lion BioSCOUT implementation of the PSI-Blast algorithm. The query was the SCIP-1 polypeptide sequence, and the NR database provided with Lion BioScout was searched. Parameters were set to match as closely as possible the defaults recommended by NCBI.

The best PSI-Blast hits found in the database for SCIP-1 were the group of archeal and eubacterial hypothetical proteins found in earlier BLASTP searches. As the PSI-Blast search progressed, however, another group of proteins entered the alignments. Table 2 shows the 14 best hits from the PSI-Blast search other than the hypothetical proteins. It is notable that the areas of alignment are found across the entire length of these proteins (data not shown).

The proteins found in the PSI-Blast search fall into a class of flowering-related plant protein (CEN and others), as well as some phosphatidylethanolamine-binding proteins (PEBP). The CEN-related proteins are known to be related to a class of phosphatidylethanolamine-binding proteins (PEBP). The alignment of the SCIP-1 protein with both the CEN proteins and PEBP suggests that SCIP-1 may be related to this class of PEBP proteins. By analogy to other reported PEBP-type proteins, SCIP-1 may play a role in signaling, in membrane transduction, or in the regulation of cell death.

TABLE 2

Selected hits from PSI-Blast search with SCIP-1 against the NR protein database. From the entire set of PSI-Blast results, the 14 best hits were selected that were not from bacteria, and that had functional annotations associated with the molecule.

| Hit (Accession Numbers) | PSI-Blast expectation | Description | Reference |
| --- | --- | --- | --- |
| trembl\|AB017525\|AB017525_1 | 1e-29 | gene: "BNTFL-1"; *Brassica napus* BNTFL-1 gene, complete cds | Mimida et al. (1999) Plant Science 142:155–162 |
| swiss\|P54186\|D1_ONCVO | 1e-29 | D1 PROTEIN (FRAGMENT) from *Onchocerca volvulas* (nematode) | Erttmann et al. (1996) Gene 174:203–7 |
| trembl\|AB017528\|AB017528_1 | 3e-29 | gene: "BRTFL1-1"; *Brassica rapa* BRTFL1-1 gene, complete cds | Mimida et al. (1999) Plant Science 142:155–162 |
| trembl\|AF145261\|AF145261_1 | 1e-28 | gene: "CET4"; product "CEN-like protein 4"; Nicotiana tabacum CEN-like protein 4 (CET4) mRNA, complete cds. | Amaya et al. (1999) Plant Cell 11:1405–1417 |
| trembl\|D87130\|ATD130_1 | 2e-28 | gene: "terminal flower1"; product: "terminal flower1"; *Arabidapsis thaliana* DNA for terminal flower1, complete cds. | Ohshima et al. (1997) Mol Gen Genet 254:186–94 |
| trembl\|U84140\|U84140_1 | 4e-28 | gene: "sp"; product: "self-pruning protein"; *Lycopersicon esculentum* self-pruning protein (sp) mRNA, complete cds | Pnueli et al. (1989) Development 125:1979–1989 |
| trembl\|B027456\|AB027456_1 | 1e-27 | gene: "CiFT"; *Citrus unshiu* CiFT mRNA, complete cds. | Kobayashi et al. (1999) Science 286:1960–2 |
| swiss\|O16264\|PBPH_CAEEL | 3e-27 | PHOSPHATIDYLETHANOLAMINE-BINDING PROTEIN HOMOLOG F40A3.3. | Unpublished |
| trembl\|AB027506\|AB027506_1 | 6e-27 | gene: "TSF"; product: "TSF"; *Arabidopsis thaliana* TSF (TWIN SISTER OF FT) mRNA, complete cds | Kobayashi et al. (1999) Science 286:1960–2 |
| swiss\|Q41261\|CEN_ANTMA | 3e-26 | CENTRORADIALIS PROTEIN. [Antirrhinum = snapdragons, mRNA, 929 nt]. | Bradley et al. (1996) Nature 379:791–7 and Bradley et al. (1997) Science 275:80–83. |
| trembl\|AB027504\|AB027504_1 | 5e-26 | gene: "FT"; product: "FT"; *Arabidopsis thaliana* FT (FLOWERING LOCUS T) mRNA, complete cds | Kobayashi et al. (1999) Science 286:1960–2 |
| trembl\|AF159882\|AF159882_1 | 8e-26 | gene: "Fdr2"; product: "Cen-like protein FDR2"; Oryza sativa Cen-like protein FDR2 (Fdr2) mRNA, complete cds | Unpublished |
| trembl\|AB024712\|AB024712_1 | 1e-24 | gene: "ATC"; *Arabidopsis thaliana* ATC (centroradialis) gene, complete cds, strain:Landsberg | Unpublished |

TABLE 2-continued

Selected hits from PSI-Blast search with SCIP-1 against the NR protein database. From the entire set of PSI-Blast results, the 14 best hits were selected that were not from bacteria, and that had functional annotations associated with the molecule.

| Hit (Accession Numbers) | PSI-Blast expectation | Description | Reference |
| --- | --- | --- | --- |
| tremb1\|D16111\|HSHRPBP__1 | 1e-23 | product: "human homologue of rat phosphatidylethanolamine binding protein"; Human mRNA for human homologue of rat phosphatidylethanolamine binding protein, complete cds | Hori et al. (1994) Gene 140:293–4 |

Example 2

Northern Analysis of mRNA Levels of Disease Resistance Genes Following Biotic and Abiotic Stresses The expression of many plant defense genes are induced by biotic and abiotic stresses. Salicylic acid (SA), Jasmonic acid (JA), and $H_2O_2$ have been implicated in playing a central role of plant disease resistance and systemic acquired resistance. Oxalic acid (OA), a compound produced by Sclerotinia and many other fungal pathogens in planta, plays an important role in the disease infection process.

The expression of LOX, rhoGAP, SCIP-1, and ADH mRNA in the presence of compounds known to induce either systemic acquired resistance or disease response was determined. Six-week-old sunflower leaves were sprayed until runoff with 5 mM SA, 45 $\mu$M JA, 5 mM of oxalic acid, and 5 mM $H_2O_2$. Leaf samples from chemical treated plants were collected at 0, 6, 12, and 24 hours after foliar application.

Northern analysis indicated that there was a significant increase in the steady-state levels of ADH mRNA in SA and $H_2O_2$ treated leaves (data not shown). The highest level of ADH mRNA expression was detected at 6 hours after application of $H_2O_2$ and 12 hours following the administration of SA. There was about a 2-to 3-fold increase in rhoGAP transcripts in response to both the $H_2O_2$ and OA application (data not shown). The mRNA levels of SCIP-1 increased upon treatment with OA.

JA, a product of the LOX pathway, significantly induced the steady-state levels of LOX mRNA. Therefore, LOX mRNA seems to be controlled by a positive feedback loop. In contrast, foliar application of SA and $H_2O_2$ repressed the expression of LOX mRNA in sunflower. Northern and RNA profiling results revealed that sunflower LOX mRNA was elevated by Sclerotinia infection and oxalic acid, a pathogenic factor produced by the fungus (data not shown).

The effects of Sclerotinia infection and oxox on SCIP-1, rhoGAP, and ADH mRNA levels was also determined. RNA levels in Sclerotinia-infected sunflower and oxox-transgenic sunflower plants were determined using Northern analysis. RNA was isolated from leaves from 6-week-old non-transformed SMF3 plants and from 6-week-old oxox-transgenic plants. Steady state levels of SCIP-1 mRNA significantly increased in 6-week-old leaf tissue from the oxox-transgenic plants as compared to the control SMF3 leaf samples. RNA was also isolated from stem tissue from 6-weekold non-transformed SMF3 plants and from 6-week-old oxox-transgenic plants. An increase in steady state levels of SCIP-1 mRNA was not detected in the stem tissue (data not shown).

RNA was also isolated from 6-week-old SMF3 plants that were infected 5-days prior to sample collection with Sclerolinia. The steady state levels of SCIP-1 RNA following Sclerolinia infection increased significantly when compared to RNA levels from uninfected leaf tissue. No change in SCIP-1 RNA levels was seen in the stem tissue following Sclerotinia infection (data not shown).

Induction of SCIP-1, ADH, and rhoGAP expression in oxox-transgenic sunflower leaf and stem tissue during development was analyzed. RNA was isolated from leaf and stem tissue from SMF3 plants and oxox-transgenic sunflower plants at 4-week-old, 6-week-old, and 8-week-old stages. Northern blot analysis using RNA samples from SMF3 sunflower plants and samples from oxox-transgenic plants demonstrated SCIP-1 RNA levels increased in leaf tissues in the oxox-transgenic sunflowers. The increase in SCIP-1 RNA levels was most significant at the 8-week-old stage. No detectable induction of SCIP-1 was seen in the stem tissue.

The steady-state-level of ADH mRNA is much higher in stem than in leaf tissue. Adh expression was induced in 8-week-old oxox-transgenic leaf tissue. However, its as expression was repressed in oxox-stem tissue. CuraGen QEA assay results indicate that Adh expression was induced by Sclerolinia infection in stem and leaf tissues (data not shown).

In the leaf tissue, rhoGAP mRNA level was induced by oxox expression at the 4-week-old stage, and then was repressed with development. In stem tissue, rhoGAP expression was slightly induced by oxox (data not shown).

LOX expression in response to wounding and the ABA signal was determined. Six-week-old sunflower plants (SMF3) were sprayed with 100 $\mu$M ABA until the chemical solution started to run off the leaves. For the wounding experiment, each wounded leaf was crushed by a hemostat 20 times and three leaves were treated from each plant. At each time point, six leaves were collected from two treated plants and immediately frozen in liquid $N_2$. Total RNA was isolated and Northern analysis was performed. Northern blot analysis indicated that wounding significantly induced the steady state levels of LOX mRNA. The peak of the LOX mRNA accumulation was detected at 6 hours after wounding and high levels of LOX expression was maintained through 72 hours after initial treatment. ABA treatment showed only a slight induction of LOX expression at 12 hours after treatment (data not shown).

Example 3

Transformation and Regeneration of Maize Transgenic Plants

The nucleotide sequences of the present invention can be used to transform sunflower, maize, or other plants using Agrobacterium or particle-gun methods. Examples 3, 4, and 5 provide methods for sunflower, maize, and soybean transformations.

Figure 2:
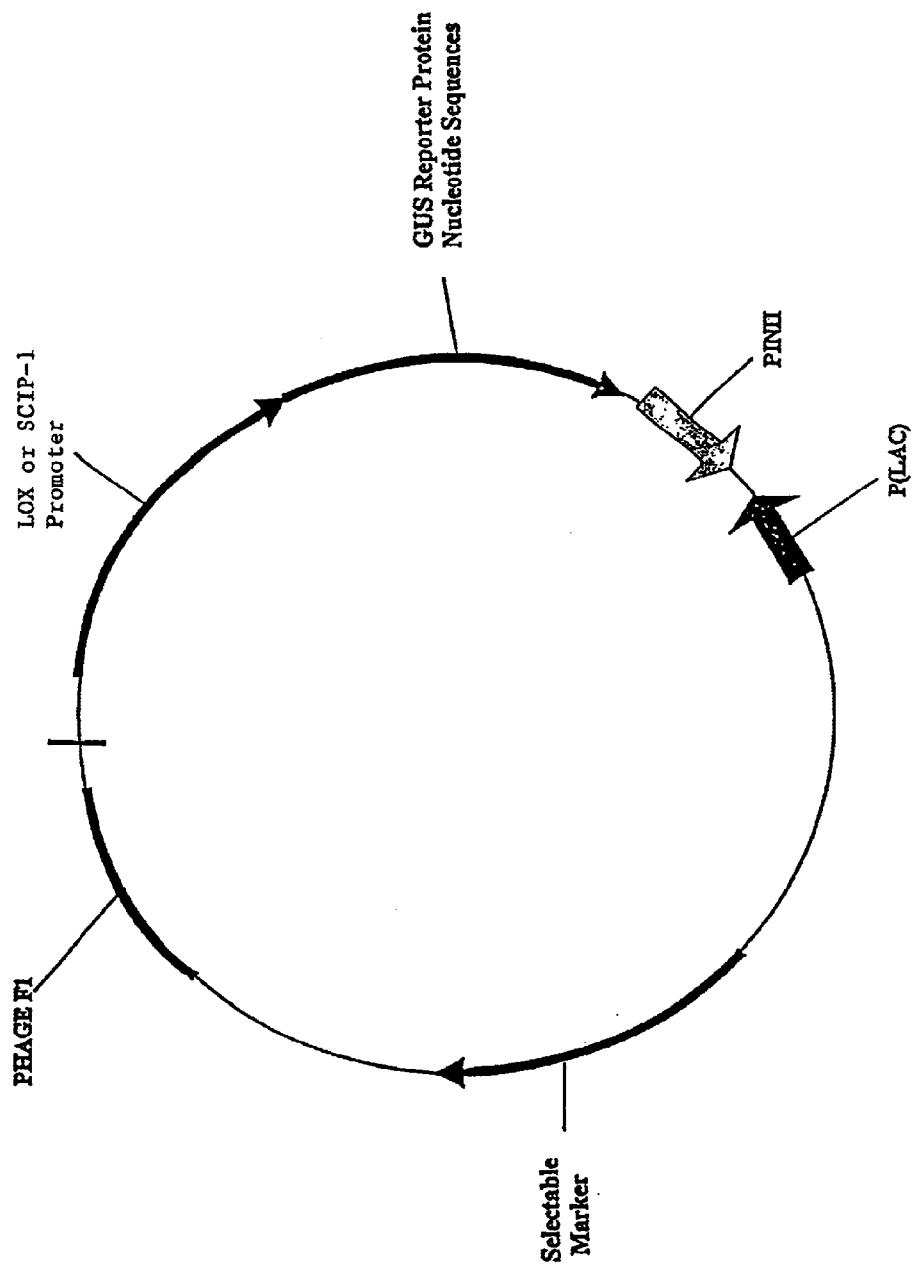
FIG. 2 schematically illustrates an expression vector used for plant transformation containing the LOX or SCIP-1 promoter nucleotide sequences operably ell linked to the nucleotide sequences encoding the GUS reporter protein.

Immature maize embryos from greenhouse donor plants are bombarded with a plasmid containing a rhoGAP, LOX, ADH or SCIP-1 nucleotide sequence operably linked to a ubiquitin promoter (FIG. 1). The plasmids also contain the selectable marker gene PAT (Wohlleben et al. (1988) *Gene* 70:25–37) that confers resistance to the herbicide Bialaphos. Transformation is performed as follows. All media recipes are given in the Appendix. Alternatively, the plant can be transformed with a plasmid comprising the LOX or SCIP-1 promoter sequences of the invention operably linked to the nucleotide sequence encoding the GUS reporter protein (FIG. 2).

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment Preparation of DNA A plasmid vector shown in FIGS. 1 or 2 is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment Particle Gun Treatment The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subculture every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established Plants are then transferred to inserts in flats (equivalent to 2.5"pot) containing potting soil and grown for 1 week in a growth chamber, subsequently grown an additional 1–2 weeks in the greenhouse, then transferred to classic 600 pots (1.6 gallon) and grown to maturity.

Plants transformed with the plasmid shown in FIG. 1 comprising the rhoGAP, LOX, ADK, or SCIP-1 nucleotide sequences are monitored and scored for altered defense response, or altered rhoGAP, LOX, ADH, or SCIP-1 activity.

Plants transformed with the plasmid shown in FIG. 2 comprising the LOX or SCIP-1 promoter sequences operably linked to the GUS reporter sequences are monitored for LOX or SCIP-1 promoter activity. Following exposure to various stimuli, such as for example, Sclerotinia and oxalic acid, LOX promoter activity is measured using the reporter gene GUS. GUS activity in various tissues is measured by a fluorogenic assay. The fluorogenic assay determines the specific activity of β-glucosidase (GUS) in various maize tissue extracts. The specific activity of the enzyme is expressed as moles of 4-methyl umbelliferone (MU) released/μg protein/hour. MU is produced when the enzyme (GUS) in plant cell extracts cleaves the glucuronide moiety from the 4-methyl umbelliferyl-β-D-glucuronide (MUG) substrate.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gekite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511),0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 m/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-l $H_2O$), sterilized and cooled to 60° C.

Example 4

Agrobacterium-mediated Transformation

For Agrobacterium-mediated transformation of maize with rhoGAP, LOX, ADH, or SCIP-1 nucleotide sequences of the invention or a nucleotide sequence operably linked to the LOX or SCIP-1 promoter sequence of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the DNA constructs of interest to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting"step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 5

Transformation and Regeneration of Sunflower Plants

The intact meristem method is used for transformation of sunflower plants and expression of the LOX, ADH, rhoGAP, or SCIP-1 nucleotide sequences as follows. Alternatively, the same method could be used to express a nucleotide sequence of interest under the control of the LOX or SCIP-1 promoter sequence of the invention.

Explant Preparation

Seeds are dehulled and surface-sterilized for 20 minutes in a 20% Chlorox™ bleach solution with the addition of two to three drops of Tween 20 per 100 ml of solution, and then rinsed three times with distilled water. Sterilized seeds are imbibed in the dark at 26° C. for 20 hours on filter paper moistened with water. Meristem explants are created by removing cotyledons and root radicle from imbibed seeds, and then culturing overnight at 26° C. in the dark on 374E medium (1×MS salts, Shepards vitamins, 40 mg/l adenine sulfate, 30 g/l sucrose, o.5 mg/l BAP, 0.25 mg/l IAA, 0.1 mg/l IAA, pH 5.6, 8 g/l phytagar). Primary leaves are then removed and explants are transferred to 374M medium (374E except 12 g/l phytagar), arranged in a manner suitable for particle gun bombardment, and cultured overnight at 26°C. in the dark.

Preparation of DNA

A plasmid vector comprising the rhoGAP, LOX, ADH, or SCIP-1 nucleotide sequences operably linked to a ubiquitin promoter is constructed (FIG. 1). Alternatively, a plasmid vector comprising the LOX promoter or the SCIP-1 nucleotide sequence operably linked to the nucleotide sequence encoding the GUS reporter protein is constructed FIG. 1). Both of these plasmids contain a kanamycin selectable marker gene. The transformation is performed as follows.

Transformation

Approximately 18.8 mg of 1.8 µm tungsten particles are suspended in 150 µl absolute ethanol, and sonicated for 2–4 seconds. After sonication, 10 µl of the suspension is dropped on the center of the surface of a macrocarrier. Each plate of meristem explants is bombarded twice with 650 psi rupture discs in the top shelf at 26 mm of Hg helium gun vacuum, using a BioRad helium gun.

The plasmid vector shown in FIG. 1 or in FIG. 2 is introduced into Agrobacterium strain EHA 105 (see above) via freeze-thawing as described by Holsters et al. (1978) Mol. Gen. Genet. 163:181–187. Actively growing, transformed Agrobacteria were maintained in shaking liquid cultures using 60A medium with kanamycin (YEP, 50 mg/l kanamycin: 10 g/l yeast extract, 10 g/l bactopeptone, 5 g/l NaCl, pH 7.0, 50 mg/l kanamycin). On the day before the Agrobacterium strain is to be used, new liquid cultures are initiated in 60A with kanamycin from the active maintenance culture. They are cultured with shaking at 26° C. until they reach an optical density (OD vis=600 nm) of about 1.0. When the cultures have established this density, they are centrifuged (6000 rpm, 5 min), the supernatant is discarded, and the pellet of bacteria is resuspended in inoculation medium (12.5 mM 2-(N-morpholino) ethanesulfonic acid, 1 g/l NH4Cl, and 0.3 g/l MgSO4, at pH 5.7), to a final calculated concentration of Agrobacteria of 4.0 at OD 600. The particle bombarded explants are inoculated with Agrobacterium by first spreading the explants apart on the 374M medium, then placing a droplet of the above suspension directly onto the top of each meristem. The explants are co-cultivated on the medium for 4 days, after which the explants are transferred to 374 C medium (GBA with 1% sucrose and with no BAP, IAA, or GA3, and supplemented with 250 µg/ml cefotaxime). The explants are cultured on this medium for about 2 weeks under 16 hours of daylight, at 26° C.

Recovering Nodes and Plants

Following the 4 days of co-cultivation time on 374M medium, the explants are transferred to 374D (374C medium with 50 mg/l kanamycin) selection medium containing kanamycin. After 2 weeks of selection, explants with associated shoots are transferred to 374C medium and selection resistant shoots are screened using NPTII ELISA. Positive shoots are removed for recovery by in vitro grafting and transformation verified by further NPTII ELISA analysis. Negative shoots are discarded. Explants with smaller shoots which could not be assayed following the 2 weeks on 374D are transferred to 374G (374E with 250 mg/l cefotaxime) for 3–4 days then back to 374C for 2 additional weeks. Assays are then done to identify positive shoots which are too small to sample in the first round and recovery initiated. Recovered positive shoots are grafted to Pioneer sunflower hybrid in vitro-grown sunflower seedling rootstock. The seeds are dehulled and surface-sterilized for 20 minutes in a 20% Chlorox™ bleach solution with two to three drops of Tween20 per 100 ml total volume, and rinsed three times with distilled water. The sterilized seeds are germinated for three days on filter paper moistened with water, then transferred into "48 Medium" (one-half strength MS salts, 0.5% sucrose, 0.3% gelrite, at pH 5.0) and grown at 26° C. at 26 in the dark for 3 days, then incubated at 16 hour day culture conditions. The upper portions of selected seedlings are removed, a vertical slice is made in each hypocotyl, and a transformed shoot is inserted into the vertical slice. The cut area is wrapped with parafilm, and after one week culture on the medium, the grafted plants are transferred to soil. In the first two weeks they are maintained under high humidity conditions to acclimatize to the greenhouse environment.

Transformed sectors of TO plants are identified by additional NPTII assays of the greenhouse established positive grafted shoots. After assay, non-transformed sectors are trimmed off to promote auxiliary bud development and auxiliary buds from transgenic sectors are recovered so as to establish the best probability to encompass the sector of transformation in germ line cells so that the transformation event is recovered in the next generation. Seed from T0 plants are collected, de-hulled, surface sterilized, and germinated on filter paper wetted with water. T1 seedlings are then sampled for NPTII ELISA by removing green cotyledon pieces followed by transfer to seedling growth medium 48P (0.1×MS salts, 0.5% sucrose, pH 5.6, 0.3% gelrite). NPTII positive, actively growing T1 seedlings are transferred at the two leaf stage to soil for growth in the greenhouse. Seed from the confirmed T1 transgenics is used to grow T2 plants.

T2 seeds are planted in a greenhouse. Positive plants are screened by NPTII assay. Various plant tissues are harvested at 80-day-old stage after planting. The harvested material is put in mini-tubes, frozen and stored at −80° C.

Plants transformed with the plasmid shown in FIG. 1 comprising the rhoGAP, LOX, ADH, or SCIP-1 nucleotide sequences are monitored and scored for an altered defense response, or a modulation in rhoGAP, LOX, ADH or SCIP-1 activity.

Plants transformed with the plasmid shown in FIG. 2 comprising the LOX promoter sequences operably linked to the GUS reporter sequences are monitored for LOX promoter activity. Following exposure to various stimuli that induce the LOX promoter, LOX promoter activity is measured by assaying for GUS activity. GUS activity in various tissues is measured by a fluorogenic assay. The fluorogenic assay determines the specific activity of β-glucosidase (GUS) in various sunflower tissue extracts. The specific activity of the enzyme is expressed as moles of 4-methyl umbelliferone (MU) released/µg protein/hour. MU is produced when the enzyme (GUS) in plant cell extracts cleaves the glucuronide moiety from the 4methyl umbelliferyl-β-D-glucuronide (MUG) substrate.

Harvested T2 tissue samples stored at −80° C. are homogenized in 400 µl lysis buffer (40 mM Phosphate, pH 7.0, 10 mM EDTA, 10 mM β-mercaptoethanol), and then centrifuged in the Jouan GR422 centrifuge for 10 minutes at 4000 rpm. The total protein concentration of the supernatant is measured using the Bio-Rad Bradford Method (Bio-RAD) with BSA as the standard protein according to manufacture's protocol. Ten µl of diluted supernatant (about 4 µg of total protein) is used for the GUS activity assay. GUS activity is assayed according to Jefferson et al. (1987) *EMBO J.* 6: 3901–3907 using MUG as substrate.

As an alternative to the intact meristem method, the split embryonic axis method may be used as described in Malone-Schoneberg et al. (1994) *Plant Science* 103:193–207, in transforming sunflower plants with either the plasmid shown in FIG. 3 or FIG. 4 and generating T2 plants. T2 seeds are planted in a greenhouse and positive plants are screened by NPTII assay. Plant tissues are harvested at 80-day-old stage after planting. The harvested material is put in mini-tubes, frozen, and stored at −80° C.

Example 6

Soybean Embryo Transformation

Soybean embryos are bombarded with a plasmid containing the SCIP-1, rhoGAP, LOX, or ADH sequences operably linked to a ubiquitin promoter (FIG. 1) as follows. Alternatively, the soybean embryos can be bombarded with a DNA construct containing the SCIP-1 or LOX promoter operably linked to a nucleotide sequence of interest (FIG. 2). To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the DNA construct can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$(2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransfromed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims

That which is claimed:

1. An isolated nucleic acid molecule comprising a nucleotide sequence having at least 95% sequence identity to the sequence set forth in SEQ ID NO: 3, wherein said sequence encodes a polypeptide having LOX activity and wherein said sequence identity to SEQ ID NO:3 is determined using the GAP algorithm using default parameters.

2. A DNA construct comprising the nucleotide sequence of claim 1, wherein said nucleotide sequence is operably linked to a promoter that drives expression in a host cell.

3. A host cell having stably incorporated into its genome at least one DNA construct of claim 2.

4. A vector comprising the nucleic acid molecule of claim 1.

5. A host cell having stably incorporated into its genome the nucleic acid molecule of claim 1.

6. An isolated nucleic acid molecule comprising a nucleotide sequence selected from the group consisting of:

(a) the nucleotide sequence set forth in SEQ ID NO: 3;

(b) a nucleotide sequence encoding the amino acid sequence set forth in SEQ ID NO: 4;

(c) the antisense nucleotide sequence of SEQ ID NO: 3.

7. A DNA construct comprising the nucleotide sequence of claim 6, wherein said nucleotide sequence is operably linked to a promoter that drives expression in a host cell.

8. A host cell having stably incorporated into its genome at least one DNA construct of claim 7.

9. A vector comprising the nucleic acid molecule of claim 6.

10. A host cell having stably incorporated into its genome the nucleic acid molecule of claim 6.

11. An isolated nucleic acid molecule comprising the cDNA insert of the plasmid deposited as Accession No. PTA-287.

12. An isolated DNA construct comprising the nucleic acid molecule of claim 11, wherein said nucleic acid molecule is operably linked to a promoter that drives expression in a host cell.

13. A host cell having stably incorporated into its genome at least one DNA construct of claim 12.

14. A vector comprising the nucleic acid molecule of claim 11.

15. A host cell having stably incorporated into its genome the nucleic acid molecule of claim 11.

* * * * *

UNITED STATES PATENT AND TRADEMARK OFFICE
CERTIFICATE OF CORRECTION

PATENT NO.   : 6,709,865 B1
DATED        : March 23, 2004
INVENTOR(S)  : Bidney et al.

It is certified that error appears in the above-identified patent and that said Letters Patent is hereby corrected as shown below:

<u>Title page,</u>
Item [73], Assignee, add -- CuraGen Corporation, New Haven, Connecticut --.

Signed and Sealed this

Second Day of November, 2004

JON W. DUDAS
*Director of the United States Patent and Trademark Office*